United States Patent [19]

Patnode et al.

[11] Patent Number: 5,518,763
[45] Date of Patent: May 21, 1996

[54] METHOD OF MAKING INDICATOR TAPES

[75] Inventors: Gregg A. Patnode, Woodbury; Donald R. Battles, Arden Hills, both of Minn.; Francois C. D'Haese, Brabantdam, Belgium; Dan J. Morse, Minneapolis, Minn.

[73] Assignee: Minnesota Mining and Manufacturing Company, St. Paul, Minn.

[21] Appl. No.: 463,219

[22] Filed: Jun. 5, 1995

Related U.S. Application Data

[62] Division of Ser. No. 257,947, Jun. 10, 1994, Pat. No. 5,460,880, which is a continuation of Ser. No. 889,647, May 28, 1992, Pat. No. 5,436,185.

[51] Int. Cl.⁶ ............................................. B05D 5/10
[52] U.S. Cl. ................... 427/208; 427/208.6; 427/208.8; 427/210; 427/261; 427/288
[58] Field of Search .............................. 427/208, 208.6, 427/208.8, 210, 261, 288

[56] References Cited

U.S. PATENT DOCUMENTS

| | | | |
|---|---|---|---|
| Re. 24,906 | 12/1960 | Ulrich | 206/59 |
| 2,532,011 | 11/1950 | Dahlquist et al. | 154/53.5 |
| 2,798,855 | 7/1957 | Hainsworth | 252/408 |
| 2,798,856 | 7/1957 | Hainsworth | 252/408 |
| 2,838,421 | 6/1958 | Sohl | 117/122 |
| 2,889,799 | 6/1959 | Korpman | 116/114 |
| 3,067,057 | 12/1962 | Dabroski | 117/68.5 |
| 3,078,182 | 2/1963 | Crone et al. | 117/68.5 |
| 3,096,202 | 7/1963 | deGroot | 117/68.5 |
| 3,098,751 | 7/1963 | Huyck | 106/20 |
| 3,152,940 | 10/1964 | Abel et al. | 156/157 |
| 3,258,312 | 6/1966 | Olson | 23/232 |
| 3,288,718 | 11/1966 | Carumpalos | 252/408 |
| 3,311,084 | 3/1967 | Edenbaum | 116/114 |
| 3,360,337 | 12/1967 | Edenbaum | 23/253 |
| 3,360,338 | 12/1967 | Edenbaum | 23/253 |
| 3,360,339 | 12/1967 | Edenbaum | 23/253 |
| 3,386,807 | 6/1067 | Edenbaum | 23/253 |
| 3,441,430 | 4/1969 | Peterson | 117/68.5 |
| 3,523,011 | 8/1970 | Bhiwandker et al. | 23/253 |
| 3,627,469 | 12/1971 | Cheng | 23/232 |

(List continued on next page.)

FOREIGN PATENT DOCUMENTS

| | | | |
|---|---|---|---|
| 0069037 | 1/1983 | European Pat. Off. | A61L 2/26 |
| 0282178 | 9/1988 | European Pat. Off. | C09D 11/00 |
| 0297451 | 1/1989 | European Pat. Off. | C09J 3/16 |
| 0352442 | 1/1990 | European Pat. Off. | C09J 133/14 |
| 0419282A1 | 3/1991 | European Pat. Off. | A61L 2/26 |
| 1370470 | 10/1974 | United Kingdom | A61L 2/26 |
| 1458553 | 12/1976 | United Kingdom | C09D 5/26 |

OTHER PUBLICATIONS

Satas, Ed., Handbook of Pressure Sensitive Adhesives, 2nd. ed. (Van Nostrand, 1989, Chapters 20–22) (no month available).

Frye, K. G., "Winding," Chapter XV, pp. 343–435. Pulp and Paper Manufacture, 3rd ed., vol. 7, Paper Machine Operations (no date available).

Primary Examiner—Bernard Pianalto
Attorney, Agent, or Firm—Gary L. Griswold; Walter N. Kirn; Jennie G. Boeder

[57] ABSTRACT

Sterilization indicator tapes utilizing moisture-resistant, water-dispersible, pressure sensitive adhesives are provided. The indicator tapes comprise a non-water-dispersible backing having a sterilization indicator thereon, which is coated on at least one side with the moisture-resistant, water-dispersible, pressure sensitive adhesive. The indicator tapes are useful to maintain a sterilization wrapper containing articles to be sterilized in a closed position during sterilization, and normal pre- and post-sterilization handling, while also providing a means to indicate if the wrapped articles have passed through a sterilization cycle. After use, the adhesives coating the indicator tapes disperse in aqueous alkali solutions, such as are found in commercial laundries, while the backing remains intact. Methods of making and using the indicator tapes are also provided.

1 Claim, 12 Drawing Sheets

U.S. PATENT DOCUMENTS

| | | | |
|---|---|---|---|
| 3,667,916 | 6/1972 | Silva et al. | 23/230 |
| 3,704,096 | 11/1972 | Verses et al. | 23/230 R |
| 3,763,117 | 10/1973 | McKenna et al. | 260/78.5 |
| 3,852,034 | 12/1974 | Gunther | 23/232 |
| 3,862,824 | 1/1975 | Chapman | 23/253 |
| 3,865,770 | 2/1975 | Blake | 260/27 |
| 3,890,292 | 6/1975 | Bohme et al. | 260/80.76 |
| 3,981,683 | 9/1976 | Larsson et al. | 23/253 TP |
| 3,992,154 | 11/1976 | Whitbourne et al. | 23/253 |
| 4,015,937 | 4/1977 | Miyamoto et al. | 23/230 |
| 4,024,096 | 5/1977 | Wachtel | 260/29.3 |
| 4,045,397 | 8/1977 | Parkinson | 260/29.3 |
| 4,070,322 | 1/1978 | Hwang et al. | 260/29.6 R |
| 4,094,642 | 6/1978 | Sumimoto et al. | 23/254 |
| 4,168,779 | 9/1979 | Yokokoji et al. | 206/439 |
| 4,188,437 | 2/1980 | Rohowetz | 428/199 |
| 4,341,680 | 7/1982 | Hauber et al. | 525/329 |
| 4,382,063 | 5/1983 | Romito et al. | 422/57 |
| 4,388,432 | 6/1983 | Eskay | 524/388 |
| 4,413,080 | 11/1983 | Blake | 524/187 |
| 4,413,082 | 11/1983 | Gleichenhagen et al. | 524/243 |
| 4,442,258 | 4/1984 | Sunakawa et al. | 524/767 |
| 4,569,960 | 2/1986 | Blake | 524/145 |
| 4,576,795 | 3/1986 | Bruso | 422/58 |
| 4,898,762 | 2/1990 | Brown et al. | 428/152 |
| 5,064,576 | 11/1991 | Suto | 252/962 |
| 5,069,754 | 12/1991 | Watanabe et al. | 162/168.2 |
| 5,125,995 | 6/1992 | D'Haese | 156/155 |

METHOD OF MAKING INDICATOR TAPES

This is a division of application Ser. No. 08/257,947 filed Jun. 10, 1994, U.S. Pat. No. 5,460,880, which is a continuation of application Ser. No. 07/889,647, filed on May 28, 1992, U.S. Pat. No. 5,436,185.

FIELD OF THE INVENTION

This invention relates to sterilization indicator tapes utilizing water-dispersible pressure sensitive adhesives and to methods of using the same.

BACKGROUND OF THE INVENTION

A variety of products such as gowns, sheets, drapes, instruments, etc. which are required during surgery, or other aseptic procedures, are used on a daily basis in the normal operation of hospitals, clinics and the like. Where such products are not pre-packaged in a sterile state, it is necessary for the hospital or clinic to sterilize them before use. Furthermore, where these products are not disposable, and are employed more than once, it is necessary that they be cleaned and otherwise prepared for subsequent use. Prior to such use, however, it is essential that such products be sterilized.

Due to the volume of materials involved, it is often necessary to sterilize and store these products for use as desired. Accordingly, there has been developed a procedure where such products, after cleaning, laundering and the like, are packaged in cloth sterilization wrappers for subsequent use, and the wrapped package is then sterilized and stored. As may be apparent, there is a potential danger in such a procedure. There is a prospect of unsterilized packages becoming mixed with sterilized packages when stored for use.

To prevent unsterilized products from being used by the physician or attendant requiring sterile materials, various types of sterility indicators which are attached to, or incorporated into, the wrapped sterilization package have been developed. This permits a user to immediately determine whether a particular package has been passed through the sterilizer. Although such sterilization indicators have, in many instances, been placed in the wrapped package or attached to the wrapped package, the most convenient way of applying such sterilization indicators is to have the sterilization indicators carried by pressure sensitive adhesive indicator tapes used for holding the cloth wrapper in a closed position prior to, during, and after sterilization of the enclosed products.

Various pressure sensitive adhesives have been used with tape backings that include appropriate color changing means to indicate if the package has been exposed to sterilization conditions. Examples of pressure sensitive adhesives employed with such indicator tapes include water insoluble natural rubber based adhesives, natural rubber and synthetic rubber blend adhesives, styrene-isoprene-styrene block copolymers with tackifying resins, vinyl ethers, and high molecular weight acrylate copolymers having minimal amounts of plasticizing monomers included therein. See e.g., U.S. Pat. Nos. 2,889,799, 3,067,057, 3,078,182, 3,311,084, and 4,188,437. Typically, these indicator tapes use a paper, fabric or film backing, and an adhesive chemistry that is resistant to softening upon exposure to heat.

Cloth sterilization wrappers may be disposed or retained after use. If retained, the soiled cloth wrappers must be cleaned after use, usually by laundering in soapy water, such as an aqueous alkali solution. These wrappers will then be used to wrap items to be sterilized. The expense of some cloth wrappers, such as treated synthetic wrappers and untreated wrappers, demands that the closure and sterilization indicator tapes not damage the wrapper after use.

The various indicator tapes referenced above are not formulated to disperse during cleaning, and in fact, if not manually removed before laundering, may permanently damage a sterilization wrapper. Specifically, the heat and chemicals associated with laundering and drying of the sterilization wrappers will cause the pressure sensitive adhesives used with the indicator tapes to flow into the fabric of the cloth wrappers, and thereby permanently damage the sterilization wrapper.

Water-dispersible pressure sensitive adhesives have been made and used for paper making and printing operations which require splicing of the end of one roll of paper to the beginning of another roll. For example, U.S. Pat. Nos. 3,865,770, 4,413,080, 4,569,960, 3,441,430, and 2,838,421 disclose such water-dispersible pressure sensitive adhesives and/or splicing tapes made therefrom. Further examples of water-soluble or water-dispersible pressure sensitive adhesive compositions, and/or tapes made therefrom, can be found in U.S. Pat. Nos. 4,413,082, 4,341,680, 4,388,432, 3,890,292, 3,763,117, 3,152,940, 3,096,202, and European Patent Publication Nos. 0 352 442 and 0 297 451. In addition, U.S. patent application Ser. No. 07/580,116 describes an autoclavable water-dispersible pressure sensitive adhesive on a dispersible backing for use as a means to adhere cloth to cloth or cloth to skin in areas where high amounts of fluid would be present.

To date, no indicator tapes utilizing water-dispersible, pressure sensitive adhesives exist. Thus, present indicator tapes must be removed from sterilization wrappers or other garments prior to laundering to avoid permanent damage to such articles.

SUMMARY OF THE INVENTION

The present invention uses water-dispersible pressure sensitive adhesives to form sterilization indicator tapes which retain pressure sensitive adhesive properties after or during exposure to moisture and/or heat likely to be encountered in a sterilization process. Typically, the indicator tapes of the present invention are used to both close a sterilization wrapper used to contain articles to be sterilized, and to indicate that the wrapped package has passed through a sterilization cycle. However, the indicator tapes of the present invention do not need to be removed from the sterilization wrappers prior to laundering. Thus, when the wrappers containing the indicator tapes are laundered, the water-dispersible, pressure sensitive adhesives coating the indicator tapes disperse upon immersion in the aqueous alkali laundering solutions, while the tape backing containing the sterilization indicator, such as an indicator ink, stays intact. Preferably, but not necessarily, the immersion of the indicator tapes occurs at elevated temperatures and considerable agitation, such as prevalent during a hot water laundry cycle.

In particular, the present invention provides an indicator tape comprising a non-water-dispersible backing having opposing sides and including thereon a sterilization indicator, and a moisture resistant, water-dispersible, pressure sensitive adhesive coated on at least one of the opposing sides of the backing. Preferably, the sterilization indicator comprises an indicator ink in combination with a binder. It is also preferable that the indicator tape be capable of maintaining a wrapped bundle of articles in a closed position during sterilization, and normal pre- and post-sterilization handling.

The present invention also provides a method making an indicator tape comprising: (a) providing a non-water-dispersible backing having opposing sides; (b) imprinting a sterilization indicator comprising an indicator ink in combination with a binder on one of the sides of the backing, said indicator ink being capable of undergoing a color change when exposed to sterilization conditions; and, (c) coating a moisture-resistant, water-dispersible, pressure sensitive adhesive on the opposing side of the backing.

The present invention further provides a method of using an indicator tape as a wrapper closure comprising: (a) providing an indicator tape comprising a non-water-dispersible backing having opposing sides and including thereon a sterilization indicator, with a moisture-resistant, water-dispersible, pressure sensitive adhesive coated on at least one of the opposing sides of the backing; and, (b) applying the indicator tape to a sterilization wrapper containing a bundle of articles such that the bundle will remain substantially closed during sterilization, and normal pre- and post-sterilization handling.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

DEFINITIONS

For the purposes of this invention:

"Non-water-dispersible backing" refers to a backing that will maintain sufficient physical integrity upon exposure industrial laundry conditions, such that the sterilization indicator contained thereon will not separate from said backing.

"Normal and Pre- and Post-Sterilization handling" refers to handling of wrapped bundles or packs that would likely occur in the day to day operation of hospitals, clinics, laundries and the like. This can include loading of packs into and out of sterilizers, placement of packs into storage, and movement of packs throughout and inbetween institutions.

"Sterilization Wrapper" or "Wrapper" refers to a covering, typically made of cloth, used to wrap an item or items to be sterilized by steam, gas, etc., and in fact may be formed by the outer side of an item to be sterilized. Preferably, but not necessarily, the sterilization wrapper is reusable. Cloth is defined in its broadest sense to be fabric or material formed by weaving, knitting, knotting, pressing, bonding, crocheting, interlocking, interlacing, melt-blowing, or felting of natural or synthetic yarns, filaments, or fibers. Nonlimiting examples of cloth include woven, knitted or non-woven fabrics and webs, used as sterilization wrappers.

BRIEF DESCRIPTION OF THE DRAWINGS

The invention may be further illustrated by reference to the accompanying drawings wherein.

DETAILED DESCRIPTION OF EMBODIMENTS OF THE INVENTION

Indicator Tapes

Figure 1:
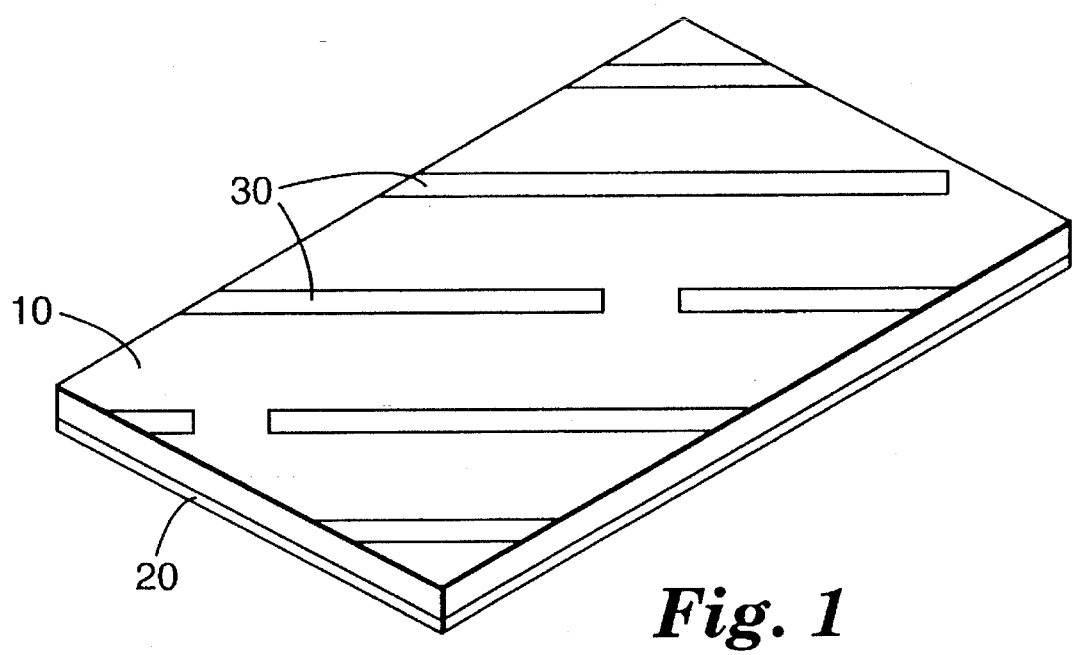
FIG. 1 is an expanded view of an embodiment of an indicator tape according to the present invention.

FIG. 1 illustrates a preferred indicator tape according to the present invention. The indicator tape includes a non-water-dispersible backing 10 that is coated with a layer of moisture-resistant, water-dispersible, pressure sensitive adhesive 20. Markings formed of a sterility indicator 30, such as a sterilization indicator ink, are printed on the backing 10. While the sterility indicator 30 is printed in a diagonal pattern in FIG. 1, it will be appreciated that any pattern, and/or variations in total surface area covered, could be encompassed by the printed sterility indicators 30 upon the non-water-dispersible backing 10.

Water-Dispersible Pressure Sensitive Adhesive Components
Pressure Sensitive Adhesive Copolymer The indicator tapes of the present invention utilize a moisture-resistant, water-dispersible, pressure sensitive adhesive to coat at least one side of a non-water-dispersible backing with a sterilization indicator thereon. In this regard, it is preferred that the water-dispersible adhesive comprise an acrylate-based adhesive copolymer in combination with a plasticizer.

In a preferred embodiment, the acrylate-based adhesive copolymer is comprised of about 50–85 weight percent of at least one monomeric acrylic acid ester of non-tertiary alkyl alcohol having 2–8 carbon atoms and correspondingly about 50–15 weight percent of a vinyl carboxylic acid monomer. Of the acrylic acid esters of non-tertiary alkyl alcohols, butyl acrylate is preferred. Of the vinyl carboxylic acids, acrylic acid is preferred. The adhesive copolymer desirably may comprise about 60–80 weight percent of butyl acrylate and correspondingly about 40–20 weight percent of acrylic acid. Preferably, the adhesive copolymer of butyl acrylate and acrylic acid has a weight percent ratio of 75:25.

The adhesive copolymer should have a sufficient inherent viscosity to provide appropriate adhesion to a sterilization wrapper. In this regard, the adhesive copolymer should have an inherent viscosity of from about 1 g/dl to about 3 g/dl. Desirably, the inherent viscosity range for the copolymer is between about 1.2 g/dl and 2.3 g/dl, and more preferably between about 1.2 g/dl and 1.3 g/dl.

Plasticizer

The plasticizer component of the water-dispersible, pressure sensitive adhesive may comprise one or more water-dispersible or water-soluble plasticizers, or a combination of water-soluble and water-dispersible plasticizers. Nonlimiting examples of suitable water-dispersible or water-soluble plasticizers include a free acid or a sodium salt of a complex organic phosphate ester, or a colophony (rosin) ester having a glass transition temperature (Tg) lower than the Tg of the pressure sensitive adhesive copolymer. Desirably, the plasticizer may be a poly(oxy-1,2-ethandiyl), alpha-(nonylphenyl)-omega-hydroxy-phosphate plasticizer, RHODAFAC PE-510™ (Rhone Poulenc, Cranbury, N.J.; formerly made by GAF Corporation, as GAFAC PE-510™); or a poly(oxy-1,2-ethandiyl), alpha-nonylphenyl-omega-hydroxy-phosphate plasticizer, such as RHODAFAC RE-410™(Rhone Poulenc; formerly made by GAF Corporation as GAFAC RE-410™), or a combination thereof.

Plasticizers are chosen to optimize adhesion properties to a given fabric substrate. Specifically, the plasticizers used in the water-dispersible pressure sensitive adhesive compositions of the present invention should be selected based on their ability to increase the flow of the pressure sensitive adhesive copolymer into the weave of the sterilization wrapper. In this regard, the RHODAFAC PE-510™is a particularly preferred plasticizer according to the present invention.

The tackifier is an optional additive to the water-dispersible pressure sensitive adhesive. If present, the tackifier is preferably a resin such as an aromatic hydrocarbon resin, or a colophony (rosin) acid compatible with acrylate copolymers. Suitable tackifier resins for acrylate copolymers are described in Satas, Ed., Handbook of Pressure Sensitive Adhesives, 2nd. Ed., (Van Nostrand, 1989), Chapters 20–22, the disclosure of which is incorporated by reference. A preferred colophony acid tackifier is FORAL AX™ (Hercules Corporation, Wilmington, Del.).

Controlling Properties of the Pressure Sensitive Adhesive

The water-dispersible, pressure sensitive adhesive is the blended product of 100 parts by weight of the adhesive copolymer, from about 10 to about 250 parts by weight of one or more plasticizers, optionally from 0 to about 100 parts by weight of an acrylate-compatible tackifier, and sufficient molar amounts, if any, of a neutralizing agent in order to control neutralization of the pressure sensitive adhesive to maintain optimal properties of withstanding sterilization conditions and initial adhesion to sterilization wrappers.

Desirably, the pressure sensitive adhesive is the blended product of 100 parts by weight of the adhesive copolymer, from about 80 to about 150 parts by weight of plasticizer, from about 20 to about 60 parts by weight of an acrylate-compatible tackifier, and sufficient molar amounts of a neutralizing agent, if any, in order to control neutralization of the pressure sensitive adhesive so as to maintain moisture resistance during and after sterilization, provide needed adhesion and strength for pre- and post-sterilization handling of wrapped bundles, and still provide water dispersibility during cleaning.

Preferably, for each 100 parts by weight of the adhesive copolymer, the plasticizer may comprise about 120 parts by weight and the tackifier may comprise about 25 parts by weight.

Variation of the amounts of the components blended to form the water-dispersible-pressure sensitive adhesive of the present invention can be used to control the effective properties of the adhesive, both during sterilization, and with respect to normal pre- and post-sterilization handling. For example, variation in the amount of incorporated plasticizer, the coating weight of the adhesive, and the amount of neutralizing agent employed to neutralize the acid groups of the adhesive can be used to increase the adhesion of the indicator tapes to the sterilization wrappers.

If used, the neutralizing agent may be one or more alkali metal hydroxides present in an amount sufficient to cause the pressure sensitive adhesive adhesion properties to withstand steam sterilization, (typically 6 minutes at 134° C. at 100% humidity at 2 bar pressure) or ethylene oxide sterilization (typically 30 minutes at 37° C. at 2 bar pressure), and normal pre- and post-sterilization handling. Also, the pressure sensitive adhesive must have sufficient dispersibility in an aqueous alkali solution after the cloth sterilization wrapper has been used.

If used, the neutralizing agent is preferably present in a molar amount sufficient to neutralize not more than 50% of the adhesive copolymer acid moiety. However, higher percent neutralization can be used, as the non-dispersible backing prevents moisture penetration into the adhesive, and thereby prevents pre-mature dispersal of the adhesive. It is preferred to keep the percent neutralization less than 100% as free base can migrate and interact with many of the ink chemistries used as sterilization indicators. While the plasticizer and tackifier may have acid moieties therein, the present invention finds that the base moiety is more apt to neutralize the adhesive copolymer acid moiety because the dissociation constant (pKa) of the adhesive copolymer acid moiety in the solvent used to prepare the pressure sensitive adhesive is 2.5 times higher than the pKa of the preferred plasticizer and 7 times higher than the pKa of the preferred tackifier.

Preferably, to achieve a balance of the functional properties of initial adhesion, wrapper closure, and moisture resistance to sterilization, and ability to withstand normal pre- and post-sterilization handling, the amount of neutralizing agent present in the blended reaction product should be sufficient to neutralize from about 12.5% to about 37.5% of the adhesive copolymer acid moiety. In this regard, it has been discovered that the property of initial adhesion of the pressure sensitive adhesive to a cloth sterilization wrapper obtains a maximum between about 0% and about 25% neutralization. Post-sterilized adhesion of the pressure sensitive adhesive remains relatively unchanged with increasing neutralization of the adhesive copolymer acid moiety on both untreated 100% cotton wrappers and on 100% polyester, fluorochemically treated wrappers. All formulations of the adhesive were completely dispersible in an industrial laundry cycle.

A further means to increase the initial adhesion of the indicator tapes of the present invention to a sterilization wrapper it to increase the amount of plasticizer in the adhesive composition. In this regard, a plasticizer level of about 120 parts by weight of the preferred PE-510 plasticizer has proven most effective at increasing the initial adhesion of the indicator tapes to the wrappers. However, there is a limit to the ability to increase plasticizer levels in the adhesive composition. Specifically, too high of a plasticizer level will result in a loss of cohesive properties of the water-dispersible adhesive coated on the indicator tapes of the present invention.

Yet another manner of increasing the initial adhesion of the indicator tapes of the present invention is to increase the coating weight of the adhesive coated on the indicator tape backing. In this regard, a coating of weight of from about 0.58 g/154.8 cm$^2$ to about 0.87 g/154.8 cm$^2$ has been found desirable. Furthermore, a coating weight of about 1.04 g/154.8 cm$^2$ helps facilitate the adhesion of the indicator tapes to treated sterilization wrappers, such as the fluorochemically-treated polyester WrapPel™ 2 wrappers (Standard Textile Co., Cincinnati, Ohio).

Preferably, to endure the harsh conditions of steam or ethylene oxide sterilization, yet be moisture resistant during use and be dispersible upon immersion in aqueous alkali solutions, the water-dispersible pressure sensitive adhesive should have an initial adhesion to cloth of equal to or greater than 1 Newton per 2.54 cm, a post-sterilized adhesion to cloth of greater that 2 Newton per 2.54 cm and hold the cloth sterilization wrapper closed upon exposure to a sterilization cycle and be able to withstand normal pre- and post-sterilization handling of the sterile package.

Preparation of the Water-Dispersible Pressure Sensitive Adhesive

The monomeric acrylic acid ester of non-tertiary alkyl alcohol and the vinyl carboxylic acid are copolymerized with an azobisisobutyronitrile initiator in accordance with the teaching of U.S. Pat. No. RE 24,906, the disclosure of which is incorporated by reference herein. The pressure sensitive adhesive is prepared by blending into the resulting adhesive copolymer, in order, the plasticizer, the tackifier, (if any is to be added), and the neutralizing agent, (if any is to be added). The blended pressure sensitive adhesive comprises solids in an organic solvent in the range from about 20 percent to about 60 percent solids and preferably from about 30 percent to about 50 percent solids. The preferred organic solvent system comprises ethyl acetate and methanol blended in a range from about 60:40 to about 90:10, and preferably 80:20. Alternatively, water is also added to the solvent system to provide a range of ratios of ethyl acetate:methanol:water of from about 60:35:5 to about 80:15:5.

As will be apparent from the ranges indicated above, substantial variations in composition are possible. For example, the use of higher percentages of short-chain acrylates in a copolymer tends to increase the hardness of the adhesive, decreasing its tackiness. In such event, it is desirable to use a comparatively higher percentage of plasticizer. On the other hand, high percentages of long chain acrylates increase the tackiness of an adhesive and reduce the need for plasticizers. Similarly, the higher the percentage of vinyl carboxylic acid in the copolymer, the lower the degree of neutralization necessary to insure water dispersibility. Well known acrylate monomers such as isooctyl acrylate may increase the tackiness of the ultimate adhesive and improve its adhesion to cloth sterilization wrappers.

Non-Water-Dispersible Backing and Sterilization Indicator

The non-water-dispersible tape backing can be made from any non-water-dispersible film, paper, or other material physically capable of withstanding the conditions of a given steam and/or ethylene oxide sterilization cycle. Nonlimiting examples of other suitable backings include isotactic polypropylene backings, such as disclosed in U.S. Pat. No. 4,898,762, the disclosure of which is herein incorporated by reference, as well as latex-saturated paper backings, foil backings, woven and nonwoven backings, polyolefin-based film backings, such as polyethylene backings, and also polyester film backings. Preferably, the tape backing comprises a 29 pound basis weight Kraft paper (M-2383 Smooth Crepe Semi-Bleached Kraft Saturating Paper; Mosinee Paper Corporation, Mosinee, Wis.). The Kraft paper is chosen for its ease of tearing which is an important consideration for opening a wrapped sterilized pack.

The paper backing is coated with an ink capable of changing color upon exposure to the given conditions of a sterilization cycle. Virtually any indicator ink can be used with the tape backings and water-dispersible adhesives of the present invention, as long as the ink and adhesive components do not react to cause pre-mature color development of the indicator ink. Thus, steam sterilization indicator inks, such as lead carbonate-sulfur. indicator inks, ethylene oxide sterilization indicator inks, or both types of indicator inks, can be imprinted on the tape backings of the present invention. See e.g., U.S. Pat. No. 3,667,916, the disclosure of which is herein incorporated by reference. Nonlimiting examples of suitable inks according to the present invention are disclosed in U.S. Pat. Nos. 3,386,807; 3,098,751; 3,360,337; 3,360,338; 3,360,339; 3,862,824; 3,523,011; 4,382,063; 3,258,312; 3,627,469; 3,852,034; 4,015,937; 4,094,642; 4,168,779; 5,064,576, U.K. Patent Nos. 1 458 553, and 1 370 470, and EPO Publication Number 0 282 178, the disclosures of which are all herein incorporated by reference.

The preferred ink for a steam sterilizer is a lead carbonate-sulfur system in a binder system, gravure printed in lines onto the Kraft paper backing. Preferably the ink system comprises 38% binder, 23% sulfur, 15% lacquer thinner, 23% lead carbonate, and 1% clay (available as BENTONE™ 38, NL Chemicals, Hightstown, N.J.).

Virtually any binder can be utilized with the indicator inks of the present invention, as long as the binder is capable of maintaining the utilized ink on the backing during laundering. Thus, the binder and ink must be compatible. The preferred binder system is 24% nitrocellulose ethyl alcohol (Hercules Inc., Wilmington, Del.); 3% phenol-formaldehyde resin (BECKCITE™ 24-102, BTL Specialty Resins, Toledo, Ohio); 9% tricresyl phosphate; 14% butyl alcohol; 27% xylene and 23% butyl acetate.

The ink printed Kraft paper is then strengthened using a vulcanized natural rubber-wood rosin system coated onto the paper. Preferably, the rubber system comprises 23% natural rubber (Goodyear Tire and Rubber Co., Akron, Ohio); 6% zinc oxide (Sherwin Williams, Cleveland, Ohio); 3% titanium dioxide (Type A-140, New Jersey Zinc Co., Palmerton, Pa.); 29% wood rosin (TENEX™ 36-710, Reichold Chemicals Inc., Oakbrook, Ill.); 2% calcium lithol pigment (Hercules Inc., Wilmington, Del.); and 37% mineral spirits. The preferred vulcanizer used to crosslink the rubber system is 40% white mineral oil (Type #31 USP; AMOCO Chemical Corp., Chicago, Ill.); 15% tetramethylthiuram disulfide accelerator (RT Vanderbilt Co., Norwalk, Conn.); and 45% ortho-pentamethylenethiuram sulfads (RT Vanderbilt Co.).

The printed, saturated paper backing is then treated to decrease moisture penetration of the paper. Preferably an acrylate polymer solution is utilized. The preferred solution is 19% butyl alcohol, 2.0% phosphoric acid, 9% urea, 0.8% aqueous ammonia, 31% formaldehyde, 6% isopropyl alcohol, 10% acrylic polymer (ELVACITE™ 2044; E.I. dupont Nemours, Wilmington, Del.); 9% butanol and 15% xylene.

To allow for the printed, saturated, and sealed paper backing to be coated with the water-dispersible adhesive and wound into useable form, a means of preventing the adhesive coating on one side of the printed paper from transferring to the other side must be used. Silicone or other treated release papers can be used to prevent contact of the adhesive with the non-coated side of the paper backing. Another means is to provide for a release coating or low adhesion back size on the non adhesive coated side of the tape backing. The preferred release method is a low adhesion back size. Depending on the nature of the adhesive, a urethane based low adhesion backsize can be used. The preferred low adhesion backsize to be coated on the non-adhesively coated side of the tape backing is a urethane backsize described in U.S. Pat. No. 2,532,011, the disclosure of which is herein incorporated by reference.

The non-water-dispersible backing may optionally be coated with an adhesive priming agent to increase the bond of the adhesive to the backing. The preferred priming agent is NEOPRENE™ N115, (E.I. dupont Nemours, Wilmington, Del.).

The tapes are preferably manufactured on tape rolls for continuous feeding for application to cloth sterilization wrappers.

Advantages of the Invention

The indicator tapes of the present invention can serve strictly as an indicator that a wrapped package has been sterilized, e.g., by attachment of the tape to the outside of the wrapped package. However, it is preferred that the indicator tapes of the present invention serve a dual purpose. Specifically, it is preferred that the indicator tapes be used to both hold the wrapped package in a closed position, and also provide a means to indicate completion of a sterilization cycle.

Whether utilized for a single or dual purpose, the water-dispersible pressure sensitive adhesives utilized on the indicator tapes of the present invention disperse when immersed in aqueous alkali solutions in less than about 40–60 minutes, for a range of laundering cycle times while the non-dispersible backing remains intact. Thus, the dispersible adhesive washes free from the laundered sterilization wrapper. Thus, hospitals or other users do not have to pre-maturely replace wrappers damaged by sterilization tape or adhesive residue. However, the non-water-dispersible backing ensures that indicator inks do not disperse in the wash (i.e. remain intact), and thereby prevents contamination of the laundered garments or the environment.

Furthermore, the water-dispersible pressure sensitive adhesive utilized on the indicator tapes of the present invention resist moisture and heat generated during use as a sterilization wrapper closure, and thereby avoid loss of adhesion at the time of sterilization. Even if some heat-mediated flow of the adhesive into the wrapper fabric occurs, the dispersibility of the adhesive ensures that the wrapper will not suffer any permanent damage. Also, the moisture resistance of the preferred treated paper backing of the present invention further enhances the moisture resistance of the indicator tapes, and accordingly, their ability to stay adhered to a wrapped package during a sterilization cycle.

Yet another advantage of the invention is that the water-dispersible pressure sensitive adhesive indicator tape reduces the time for processing goods to be laundered. Specifically, inspection for sterilization tape or adhesive residue does not need to take place since the pressure sensitive adhesive will disperse in the cleaning cycle.

Yet a further advantage of the invention is that the water-dispersible pressure sensitive adhesive indicator tape is tamper evident since if the tape is peeled from a sterilized wrapper it cannot be re-adhered because the adhesive remains on the wrapper thus indicating that sterility has been compromised.

Test Procedures

Initial adhesion to untreated and treated sterilization wrappers

Samples of a fluorochemically-treated polyester wrapper and a untreated 100% cotton wrapper (180 thread count) were cut into 5.08 cm by 15.24 cm strips. Example indicator tapes were applied to the untreated and treated wrappers, and were rolled twice with a 2 kg rubber roller.

One end of each of the sample wrappers was adhered to a set of jaws on an Instron Model 1122 tensile tester. (Instron Corp., Canton, Mass.), while the corresponding end of the laminated indicator tape was adhered to an opposing set of jaws of the tensile tester. The example indicator tape was peeled from the surface of the treated and untreated wrappers at a essentially a 180° peel angle. The rate of jaw movement was 25.4 cm/minute and the tensile tester recorded the force required to separate the tape laminate from the wrapper. The results were recorded in Newtons per 2.54 cm. A "B" in the column means that the backing broke or tore during the test. The initial adhesion measurement derives from the fact that the dwell time of the tape on the wrapper was short; i.e., the example tape was applied and peeled without a long residence time in between, and sterilization had not yet taken place.

Post-sterilization adhesion to untreated and treated sterilization wrappers

The same method as the initial adhesion test was used for this test, except that prior to testing, the laminate of the example indicator tapes and treated and untreated wrappers was steam sterilized at 132° C., in a 4 minute, four-pulse prevacuum cycle with a 1 minute steam dry time. The sterilizer used was an Eagle 2013 sterilizer (American Sterilizer Co., Erie, Pa.). In addition, the laminate was allowed to cool at room temperature for a minimum of 4 hours before peel testing. The results were recorded in Newton per 2.54 cm, with a "B" in the column indicating that the backing broke or tore during the test.

Pre-sterilization wrapper closure ($T_{(o)}$)

A bundle was produced by rolling towels to a cylindrical size of approximately 25.4 cm in length by 12.7 cm in diameter. The bundle of towels were then wrapped using either a 76.2 cm² untreated 100% cotton wrapper (180 thread count), or a fluorochemically-treated polyester wrapper (WrapPel™ 2; Standard Textile Co., Cincinnati, Ohio) by placing the towel cylinder diagonally on one of the wrapper corners, and rolling the cylinder towards an opposing corner, while tucking in side corners. Once completely wrapped, the bundle or pack was securely closed with an example pressure sensitive adhesive indicator tape.

The wrapped bundle was allowed to sit at room temperature (20° C., 50% R.H.) for 12 hours. The packs were inspected to assure that they remained closed. The results were recorded as follows: P means passed, bundle remains closed with no edge lift; P-E means passed, bundle remains closed with a slight lifting of the tape edge; F-P means failed, bundle is no longer closed due to tape popping off one side of pack; F-C means failed due to tape curling up and off of wrapper.

Post-sterilization wrapper closure ($T_{(A)}$)

A wrapped bundle was produced as described above for the pre-sterilization wrapper closure test, except that the bundle was immediately exposed to a steam sterilization cycle at 132° C., 7 minute, four-pulse prevacuum cycle and a 15 minute steam dry time. The packs were inspected to assure that they remained closed and the adhesive remained intact. The results were recorded as follows: P means passed, i.e. the bundle remained closed with no edge lift; P-T means, passed, with a slight tear in the backing; P-E means passed, i.e. the bundle remains closed with a slight lifting of the edge; F means failed, i.e. the bundle is no longer closed; F-T means failed due to a tear in the backing.

Dispersibility Test

Wrapped bundles were prepared using untreated 100% cotton wrappers (180 thread count) and fluorochemically-treated polyester (WrapPel™ 2) wrappers, and were sterilized as described in the Post-sterilization Wrapper Closure Test. The wrappers were removed from the bundle, with the example indicator tapes adhered to the wrappers, and laundered in a 65 lb. load in a commercial washing machine (Milnor washer, Model No. 36021BWE/AEA; Pillerin Milnor Corp., Kenner, La.). The wrappers went through a typical laundry cycle for surgical linens including: (a) two two-minute alkaline flushes, one cold and one split between hot and cold, in a 0.1% Paralate 55 GL11™ Commercial Liquid Laundry Alkali (Ecolab Inc., St. Paul, Minn.); a two-minute hot water flush, an eight-minute hot detergent/suds wash using 0.1% of Paralate 55 GLW™ Commercial Liquid Laundry Alkali, and 0.05% Kindet™ Commercial Liquid Laundry Detergent (Ecolab Inc.); a two-minute hot water flush, an eight-minute hot bleach using 0.17% of a 5.25% by weight sodium hypochlorite solution bleach (Lerro Chemical Inc., Philadelphia, Pa.); three two-minute water rinses, one hot and two split between hot and cold; a four-minute cold sour/soft rinse using 0.05% Tri Liquid Sour 55GL™ Commercial Liquid Laundry Sour (Ecolab Inc.), and 0.05% Tex Special Liquid™ Commercial Liquid Denim Lubricant/Softener (Ecolab Inc.), and a six minute extraction to remove excess liquid.

Each laundered wrapper was inspected for a pass, meaning that no adhesive residue remained on the wrapper, and the tape backing was intact (i.e., the backing did not disperse, such that the ink was still contained on the backing), or in the case of a tissue backing, dispersed; or for a fail, meaning that there was an adhesive residue on the wrapper and/or the paper backing was not intact, and/or the tissue backing had not dispersed.

Drop Test

Wrapped bundles were prepared as described in the Post-sterilization Wrapper Closure Test. The taped bundles were dropped as described in ASTM D4169-90 using Hazard Element A for a Filled Bag, and ASTM D959-80 with the following variation: the bundles were dropped from heights of 38 cm and 91.5 cm on each of the two ends and on the side of the bundle away from the tape and on the tape. The results were described as: P meaning passed, bundle still closed; P-T meaning passed, bundle still closed, but with a slight tear in the backing; F-T meaning failed, bundle opened because the backing tore; F-O meaning failed, bundle opened because the tape popped off the bundle without tearing.

The invention will be further illustrated by reference to the following non-limiting Examples. All parts and percentages are expressed as parts by weight unless otherwise indicated.

EXAMPLES 1–14

An acrylate:vinyl carboxylic acid copolymer was prepared, generally as described in U.S. Pat. No. RE 24,906. The monomers, 75 weight percent butyl acrylate/25 weight percent acrylic acid were dissolved in ethyl acetate in a 75 gallon reactor. 0.3 weight percent azobisisobutyronitrile (VAZO™ 64; E.I. dupont Nemours, Wilmington, Del.) as a polymerization initiator and 2.3 weight percent isopropanol as a chain transfer agent were added to the reactor. A nitrogen purge was introduced for two minutes at a flow rate of 1 liter/minute. The solution was held at 55° C. for about 24 hours, at which time copolymerization was 99% completed. Sufficient ethyl acetate was added to the solution to produce a system having a solids content of about 30%.

The plasticizer, the tackifier, and the alkali metal hydroxide neutralizing agent(s), if any, in a 4N 50:50 methanol and water (v/v) solution were sequentially blended into the solvent system containing the copolymer solids. Sufficient methanol and water was added to bring the system to a weight ratio of 80:15:5 ethyl acetate:methanol:water. The mixture was agitated to produce a colorless to amber, low viscosity solution.

The backing used for the indicator tapes was a 29 pound basis weight Kraft paper ("M-2383 Smooth Crepe Semi-Bleached Kraft Saturating Paper"; Mosinee Paper Corporation, Mosinee, Wis.).

The Kraft paper was gravure printed in lines with a sulfur-lead ink system in a binder system. The ink system contained 38% binder, 23% sulfur, 15% lacquer thinner, 23% lead carbonate and 1% clay ("Bertone-38"; NL Chemicals, Hightstown, N.J.). The binder system contained 24% nitrocellulose ethyl alcohol; 3% phenol-formaldehyde resin ("Beckcite 24-102"; BTL Specialty Resins, Toledo, Ohio); 9% tricresyl phosphate; 14% butyl alcohol; 27% xylene and 23% butyl acetate.

The ink printed Kraft paper was strengthened using a vulcanized natural rubber-wood rosin system coated onto the paper. The rubber system was 23% natural rubber (Goodyear Tire and Rubber Co., Akron, Ohio); 6% zinc oxide (Sherwin Williams, Cleveland, Ohio); 3% titanium dioxide ("Type A-140"; New Jersey Zinc Co., Palmerton, Pa.); 29% wood rosin ("Tenex 36-710"; Reichold Chemicals Inc., Oakbrook, Ill.); 2% calcium lithol pigment (Hercules Inc.); and 37% mineral spirits. The vulcanizer used to crosslink the rubber system was 40% white mineral oil (Type #31 USP; AMOCO Chemical Corp., Chicago, Ill.); 15% tetramethylthirum disulfide accelerator (RT Vanderbilt Co., Norwalk, Conn.); and 45% ortho-pentamethylenethiuram sulfads (RT Vanderbilt Co.).

The printed, saturated paper backing was then treated to decrease moisture penetration with a solution contained 19% butyl alcohol, 2.0% phosphoric acid, 9% urea, 0.8% aqueous ammonia, 31% formaldehyde, 6% isopropyl alcohol, 10% acrylic polymer ("Elvacite 2044"; E.I. dupont Nemours, Wilmington, Del.); 9% butanol and 15% xylene.

The pressure sensitive adhesives in the solvent system were coated on the Kraft paper at 0.68 grams per 154.8 cm$^2$ (24 in$^2$) using a standard laboratory knife coater, with drying for 15 minutes in a forced air oven at 100° C.

Table 1 shows the formulations of water-dispersible, pressure sensitive adhesives coated on Example Indicator Tapes Nos. 1–14. Tables 2 and 3 show the initial adhesion, post-sterilization adhesion, presterilization wrapper closure (T(0)), post-sterilization wrapper closure (T(A)), and dispersibility of the indicator tapes of Examples 1–14 on untreated 100% cotton wrappers and fluorochemically-treated polyester wrappers respectively.

When interpreting the results contained in Tables 1–12 and FIGS. 2–12, the data should be analyzed for trends as opposed to specific numerical values. This is due to the inherent variability in the test wrappers. This variability arises, at least in part, from the wearing effects of age, harshness of wash conditions, and residual chemicals present from laundering.

TABLE 1

Formulation of water-dispersible, preisure sensitive adhesives coated on Example Indicator Tapes Nos. 1–14.

| Ex. No. | Copolymer BA/AA (parts) | Plasticizer PE-510 (parts) | Plasticizer RE-410 (parts) | Tackifier Foral AX (parts) | Neutralization (%) | Solids (%) |
|---|---|---|---|---|---|---|
| 1 | 100 | 89 | | 23 | 00.0 | 35.0 |
| 2 | 100 | 89 | | 23 | 12.5 | 35.0 |
| 3 | 100 | 89 | | 23 | 25.0 | 35.0 |
| 4 | 100 | 89 | | 23 | 37.5 | 35.0 |
| 5 | 100 | 89 | | 23 | 50.0 | 35.0 |
| 6 | 100 | 89 | | 23 | 75.0 | 35.0 |
| 7 | 100 | 89 | | 23 | 100.0 | 35.0 |
| 8 | 100 | | 89 | 23 | 00.0 | 35.0 |
| 9 | 100 | | 89 | 23 | 12.5 | 35.0 |
| 10 | 100 | | 89 | 23 | 25.0 | 35.0 |
| 11 | 100 | | 89 | 23 | 37.5 | 35.0 |
| 12 | 100 | | 89 | 23 | 50.0 | 35.0 |
| 13 | 100 | | 89 | 23 | 75.0 | 35.0 |
| 14 | 100 | | 89 | 23 | 100.0 | 35.0 |

TABLE 2

Initial adhesion, post-sterilization adhesion, pre-sterilization wrapper closure (T(o)), post-sterilization wrapper closure (T(a)), and dispersibility of pressure-sensitive adhesive coating for Example Indicator Tapes Nos. 1–14 on T-180 untreated wrappers.

| Ex. No. | Initial Adhesion (Newton/2.54 cm) | Post-Sterilized Adhesion (Newton/2.54 cm) | Wrapper Closure T(o) (pass/fail)$^a$ | Wrapper Closure T(A) (pass/fail) | Dispersibility (pass/fail) |
|---|---|---|---|---|---|
| 1 | 5.1 | 2.5 | P-E | P | P |
| 2 | 5.8 | 2.8 | P | P | P |
| 3 | 3.9 | 3.4 | P-E | P | P |
| 4 | 2.1 | 3.2 | P-E | P | P |
| 5 | 2.6 | 2.9 | P-E | P | P |
| 6 | 1.6 | 3.0 | P-E | P | P |
| 7 | 2.7 | 2.9 | P-E | P | P |
| 8 | 1.6 | 3.3 | F-P | P | P |
| 9 | 2.4 | 1.4 | P-E | P | P |
| 10 | 2.1 | 2.1 | F-P | P | P |
| 11 | 1.6 | 4.6 | F-P | P | P |
| 12 | 1.6 | 4.8 | F-P | P | P |
| 13 | 0.7 | 4.4 | F-P | P | P |
| 14 | 1.1 | 5.0 | F-P | P | P |

$^a$P = pass, PE = pass with edge lift, FP = failed popped off

TABLE 3

Initial adhesion, post-sterilization adhesion, presterilization wrapper closure (T(o)), post-sterilization wrapper closure (T(A)), and dispersibility of pressure sensitive adhesive coating for Example Indicator Tapes Nos. 1–14 as WrapPel™ 2 fluorochemically-treated wrappers.

| Ex. No. | Initial Adhesion (Newton/2.54 cm) | Sterilized Adhesion (Newton/2.54 cm) | Wrapper Closure T(o) (pass/fail)[a] | Wrapper Closure T(o) (pass/fail) | Dispersibility (pass/fail) |
|---|---|---|---|---|---|
| 1  | 1.6 | 3.1 | F-C | P-E | P |
| 2  | 0.9 | 2.5 | F-C | F-P | P |
| 3  | 1.9 | 4.2 | P-E | P-E | P |
| 4  | 1.2 | 2.6 | F-C | P-E | P |
| 5  | 0.5 | 2.4 | F-P | P-E | P |
| 6  | 0.4 | 2.1 | F-P | P-E | P |
| 7  | 0.6 | 3.0 | F-P | P-E | P |
| 8  | 0.0 | 2.5 | F-P | F-P | P |
| 9  | 1.5 | 3.2 | F-C | P-E | P |
| 10 | 1.2 | 3.3 | F-P | P-E | P |
| 11 | 1.1 | 3.5 | F-P | P-E | P |
| 12 | 0.6 | 4.3 | F-P | P-E | P |
| 13 | 0.3 | 3.8 | F-P | P-E | P |
| 14 | 0.4 | 4.5 | F-P | P-E | P |

[a]PE = Pass with edge lift, FC = failed curled up, FP = failed popped off

Figure 2:
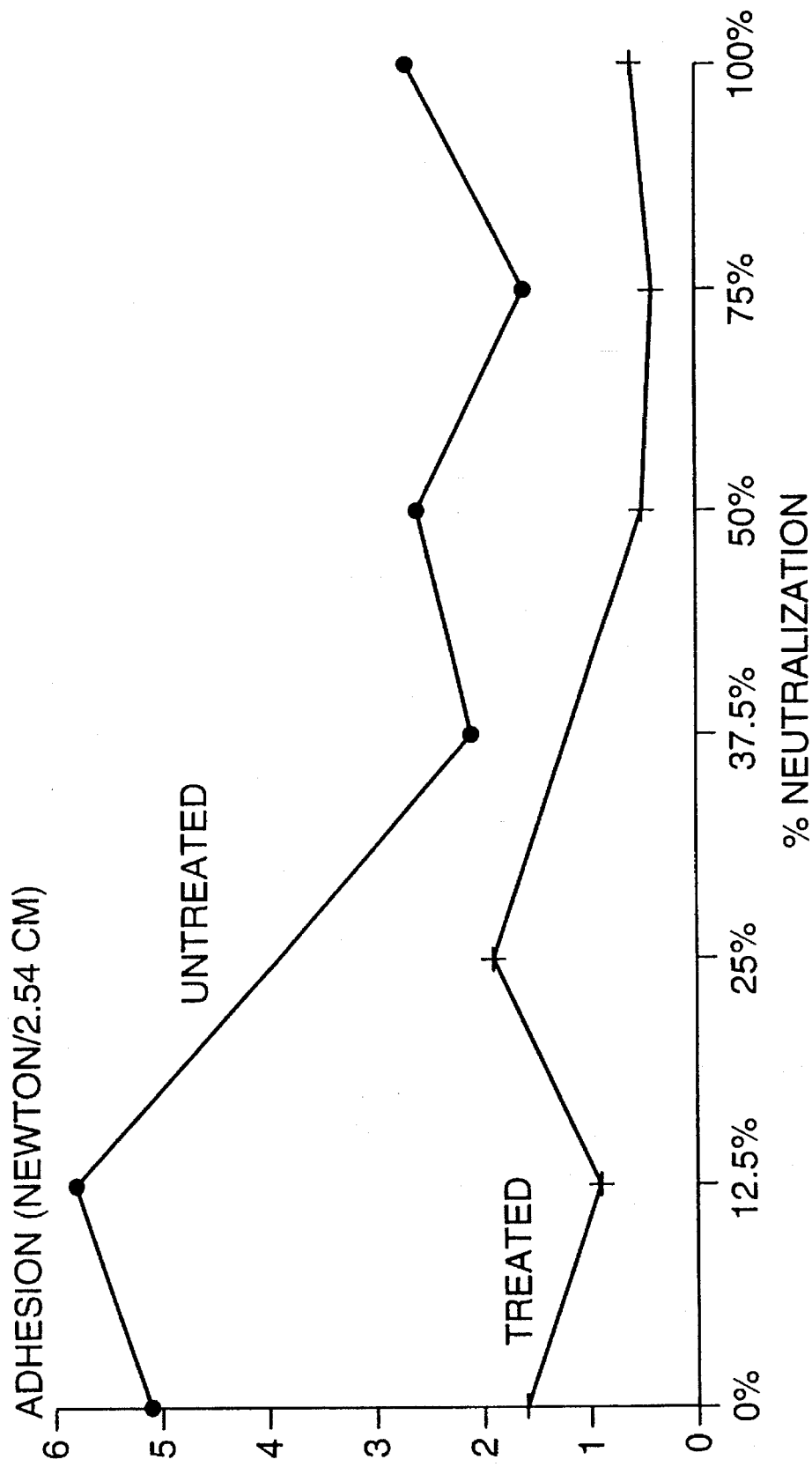
FIG. 2 is a graph of the initial adhesion of the indicator tapes of Examples 1–7 to untreated sterilization wrappers and to fluorochemically-treated polyester sterilization wrappers.
Figure 3:
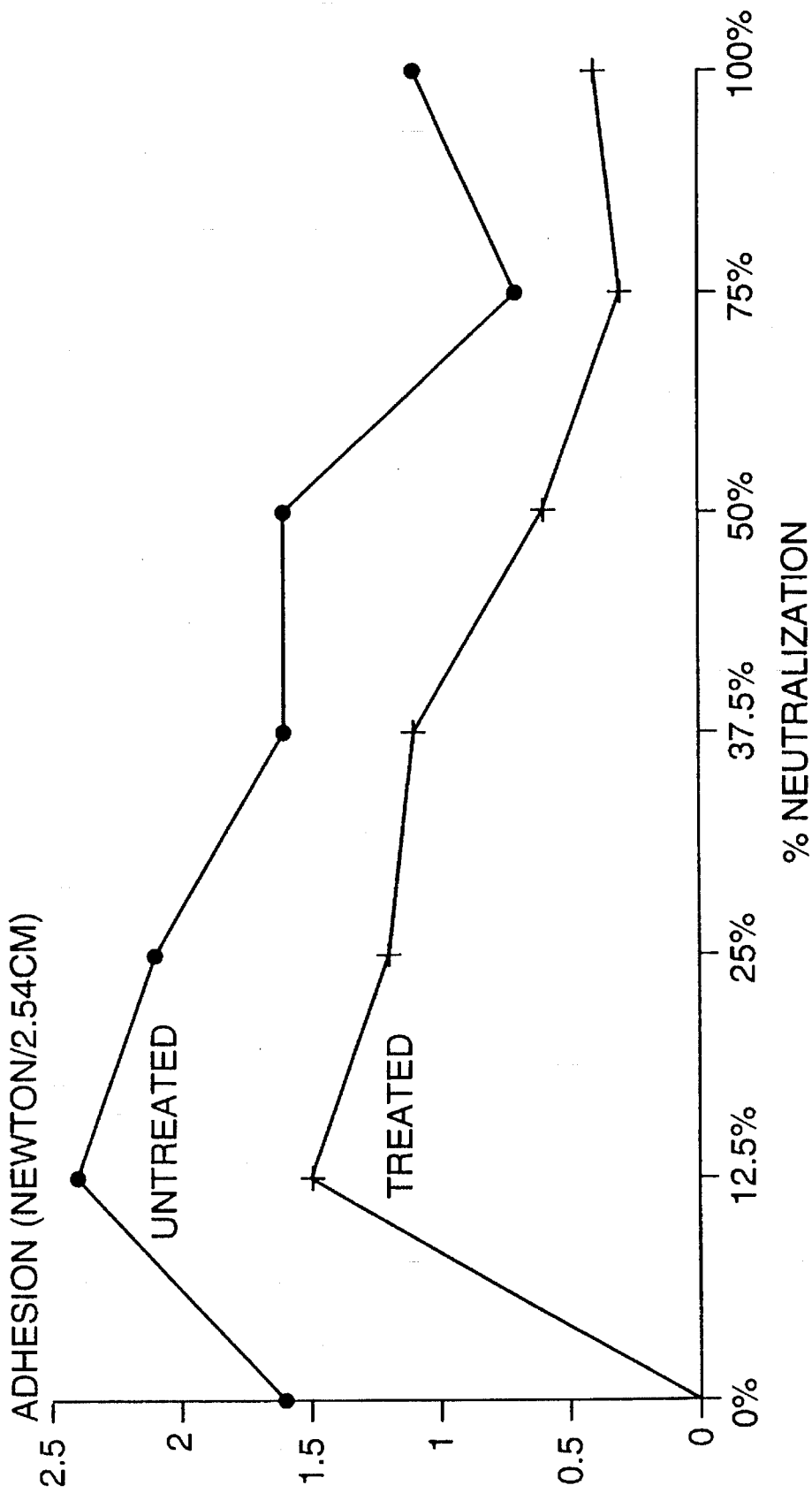
FIG. 3 is a graph of the initial adhesion of the indicator tapes of Examples 8–14 to untreated sterilization wrappers and to fluorochemically-treated polyester sterilization wrappers.
Figure 4:
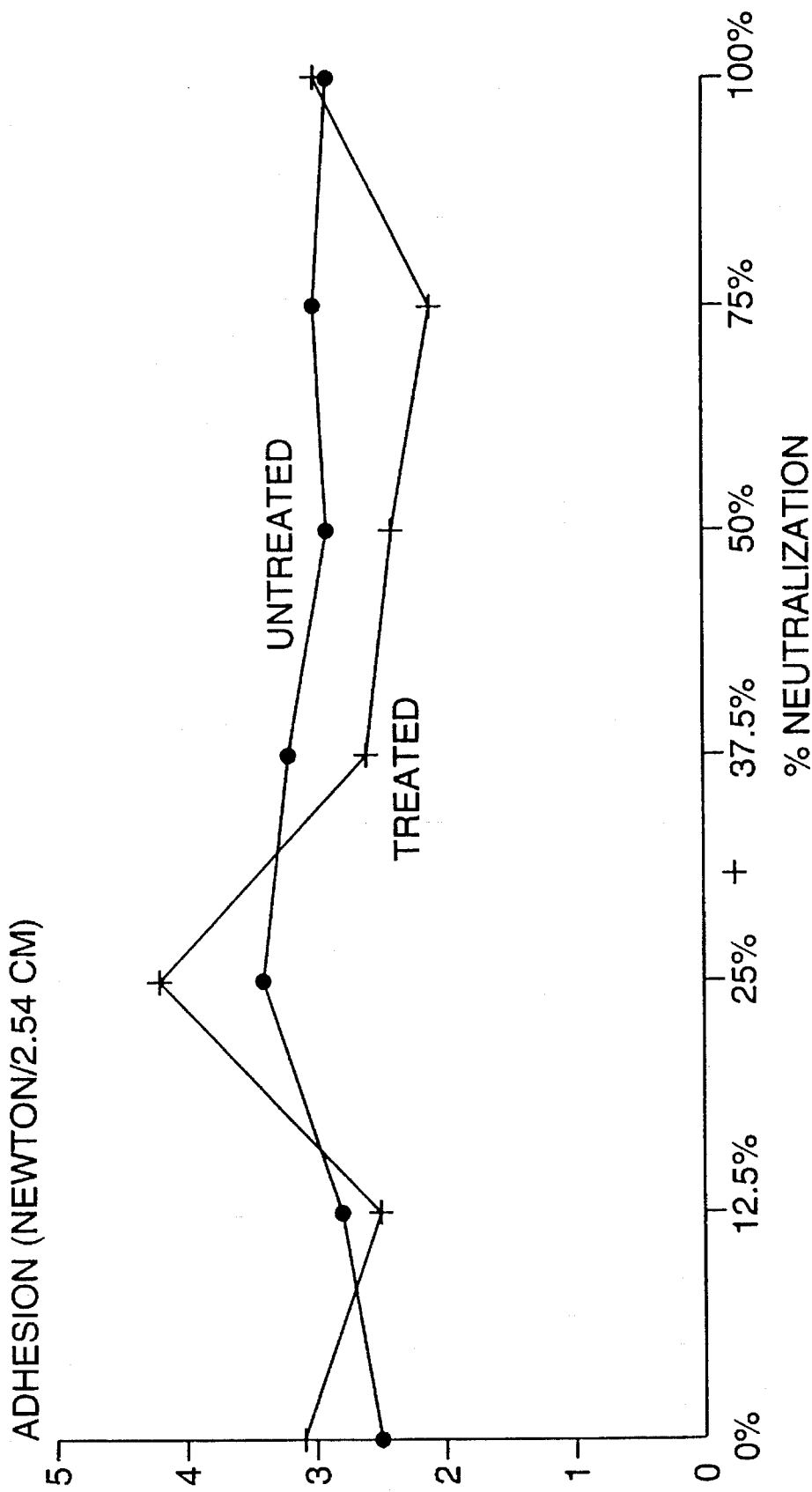
FIG. 4 is a graph of the post-sterilization adhesion of the indicator tapes of Examples 1–7 to untreated sterilization wrappers and to fluorochemically-treated polyester sterilization wrappers.
Figure 5:
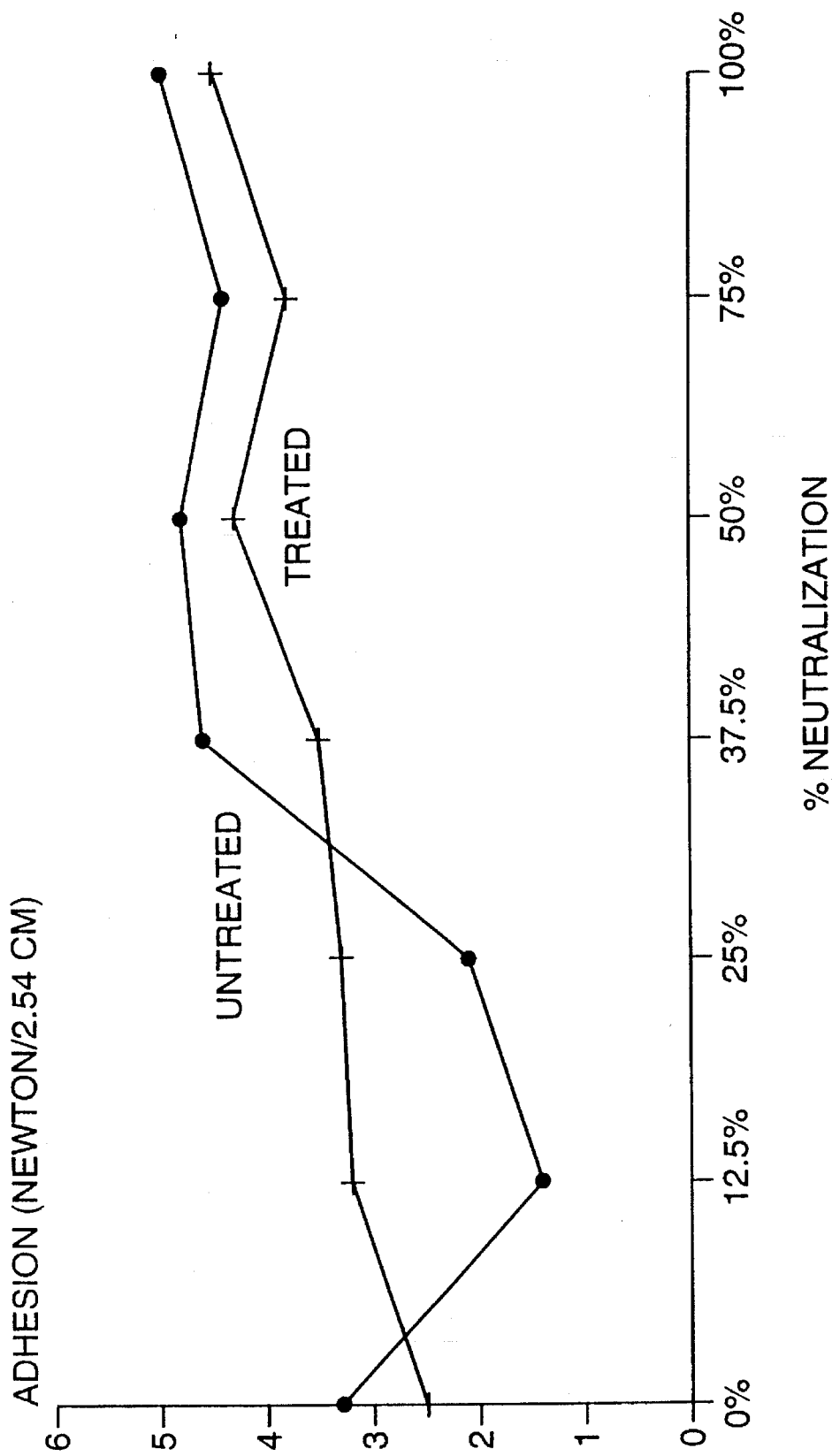
FIG. 5 is a graph of the post-sterilization adhesion of the indicator tapes of Examples 8–14 to untreated sterilization wrappers and to fluorochemically-treated polyester sterilization wrappers.

Tables 2 and 3, and FIGS. 2 and 3 show that the maximum initial adhesion of the Example Indicator Tapes occurs between 0% and 25% neutralization for both the adhesive formed with the PE-510 and the RE-410 plasticizers on both untreated 100% cotton wrappers and WrapPel™ 2 fluorochemically-treated polyester wrappers. In addition, Table 2 shows that the adhesives formed with the PE-510 plasticizer exhibit sufficient adhesion to maintain untreated wrappers in a closed position prior to sterilization. Conversely, adhesives formed with the RE-410 plasticizer, in most instances, did not exhibit sufficient adhesion to maintain untreated wrappers in a closed position prior to sterilization.

With respect to untreated wrappers, if sufficient initial adhesion can be maintained, post-sterilization wrapper closure and dispersibility of the adhesive will perform as required. This appears, at least in part, to be due the flow of the adhesives into the fabric of the wrappers when subjected to higher temperature sterilization conditions. Thus, as demonstrated in Tables 2 and 3, and FIGS. 4 and 5, post-sterilization adhesion is not as critical a factor in the successful use of the Example indicator tapes.

With respect to WrapPel™ 2 fluorochemically-treated polyester wrappers, initial adhesion is also a critical requirement. In this regard, Table 3 shows the choice of useful indicator tapes is more limited than with the untreated wrappers. Specifically, only Example indicator tape No. 3 displayed sufficient initial adhesion to maintain the WrapPel™ 2 treated wrapper in a closed position prior to sterilization. It appears that the selection of plasticizer and degree of neutralization of the water-dispersible adhesive is more limited when designing indicator tapes for treated sterilization wrappers, such as the WrapPel™ 2 wrapper.

All formulations dispersed when laundered under institutional conditions, independent of the degree of neutralization of the water-dispersible adhesive employed.

EXAMPLES 15–28

Indicator tapes 15–28 utilize the same backing and the same adhesives as Example Indicator Tapes 1–14 except the plasticizer was reduced to 84 parts from 89 parts and the tackifier was increased to 25 parts from 23 parts. Table 4 shows the formulations of water-dispersible, pressure sensitive adhesives coated on Example Indicator Tapes Nos. 15–28. Table 5 shows the initial adhesion, post-sterilization adhesion, pre-sterilization wrapper closure (T(0)), post-sterilization wrapper closure (T(A)), dispersibility and drop test results from 38 cm and 91.5 cm for the indicator tapes of Examples 15–28 on untreated 100% cotton wrappers. Table 6 shows the initial adhesion and post-sterilization adhesion of the indicator tapes of Examples 15–28 on fluorochemically-treated polyester wrappers.

TABLE 4

Formulation of water-dispersible, pressure sensitive adhesives coated on Example Indicator Tapes Nos. 15–28.

| Ex. No. | Copolymer BA/AA (parts) | Plasticizer PE-510 (parts) | Plasticizer RE-410 (parts) | Tackifier Foral AX (parts) | Neutralization (%) | Solids (%) |
|---|---|---|---|---|---|---|
| 15 | 100 | 84 | | 25 | 00.0 | 35.0 |
| 16 | 100 | 84 | | 25 | 12.5 | 35.0 |
| 17 | 100 | 84 | | 25 | 25.0 | 35.0 |
| 18 | 100 | 84 | | 25 | 37.5 | 35.0 |
| 19 | 100 | 84 | | 25 | 50.0 | 35.0 |
| 20 | 100 | 84 | | 25 | 75.0 | 35.0 |
| 21 | 100 | 84 | | 25 | 100.0 | 35.0 |

TABLE 4-continued

Formulation of water-dispersible, pressure sensitive adhesives coated on Example Indicator Tapes Nos. 15–28.

| Ex. No. | Copolymer BA/AA (parts) | Plasticizer PE-510 (parts) | Plasticizer RE-410 (parts) | Tackifier Foral AX (parts) | Neutralization (%) | Solids (%) |
|---|---|---|---|---|---|---|
| 22 | 100 | | 84 | 25 | 00.0 | 35.0 |
| 23 | 100 | | 84 | 25 | 12.5 | 35.0 |
| 24 | 100 | | 84 | 25 | 25.0 | 35.0 |
| 25 | 100 | | 84 | 25 | 37.5 | 35.0 |
| 26 | 100 | | 84 | 25 | 50.0 | 35.0 |
| 27 | 100 | | 84 | 25 | 75.0 | 35.0 |
| 28 | 100 | | 84 | 25 | 100.0 | 35.0 |

TABLE 5

Initial adhesion, post-sterilization, pre-sterilization wrapper closure (T(o)), post-sterilization wrapper closure (T(A)), dispersibility of pressure sensitive adhesive coating, and maintenance of closed wrapped bundles dropped from 38 cm and 91.5 cm for Example Indicator Tapes Nos. 15–28 using T-180 untreated wrappers.

| Ex. No. | Initial Adhesion (Newton/2.54 cm) | Post-Sterilize Adhesion (Newton/2.54 cm) | Wrapper Closure T(o) (pass/fail)[a] | Wrapper Closure T(o) (pass/fail) | Drop Test @ 38 cm (pass/fail) | Drop test @ 91.5 cm (pass/fail)[b] | Dispersibility (pass/fail) |
|---|---|---|---|---|---|---|---|
| 15 | 3.2 | 3.2 | P-E | P | P | P | P |
| 16 | 3.2 | 2.5 | P-E | P | P | P | P |
| 17 | 2.4 | 3.5 | P-E | P | P | P | P |
| 18 | 1.0 | 2.8 | F-C | P | P | P | P |
| 19 | 1.0 | 4.6 | F-C | P | P | P | P |
| 20 | 1.0 | 2.2 | F-C | I | P | P | P |
| 21 | 0.1 | 2.0 | F-P | P | P | P | P |
| 22 | 0.1 | 3.3 | F-P | P | P | F-O | P |
| 23 | 1.6 | 3.4 | F-P | P | P | P | P |
| 24 | 1.3 | 3.5 | F-P | P | P | P | P |
| 25 | 0.3 | 2.7 | F-P | P | P | P | P |
| 26 | 0.6 | 2.7 | F-P | P | P | P | P |
| 27 | >0.1 | 2.6 | F-P | P | P | P | P |
| 28 | >0.1 | 2.5 | F-P | P | P | P | P |
| | | | | | | | P |

[a]PE = pass with edge lift, FC = failed curled up, FP = failed popped off
[b]P = pass, F-O = failed by opening

TABLE 6

Initial adhesion and post-sterilization adhesion for Example Indicator Tapes Nos. 15–28 on WrapPel ™ 2 fluorochemically-treated wrappers.

| Ex. No. | Initial Adhesion (Newton/2.54 cm) | Post-Sterilized Adhesion (Newton/2.54 cm) |
|---|---|---|
| 15 | 0.6 | 1.9 |
| 16 | 1.3 | 1.7 |
| 17 | 0.7 | 1.7 |
| 18 | 0.3 | 1.4 |
| 19 | 0.1 | 1.5 |
| 20 | 0.1 | 1.8 |
| 21 | >0.1 | 1.2 |
| 22 | >0.1 | 2.2 |
| 23 | 0.5 | 2.4 |
| 24 | 0.4 | 2.8 |
| 25 | 0.1 | 2.8 |
| 26 | >0.1 | 2.2 |
| 27 | >0.1 | 1.8 |
| 28 | >0.1 | 1.8 |

Figure 6:
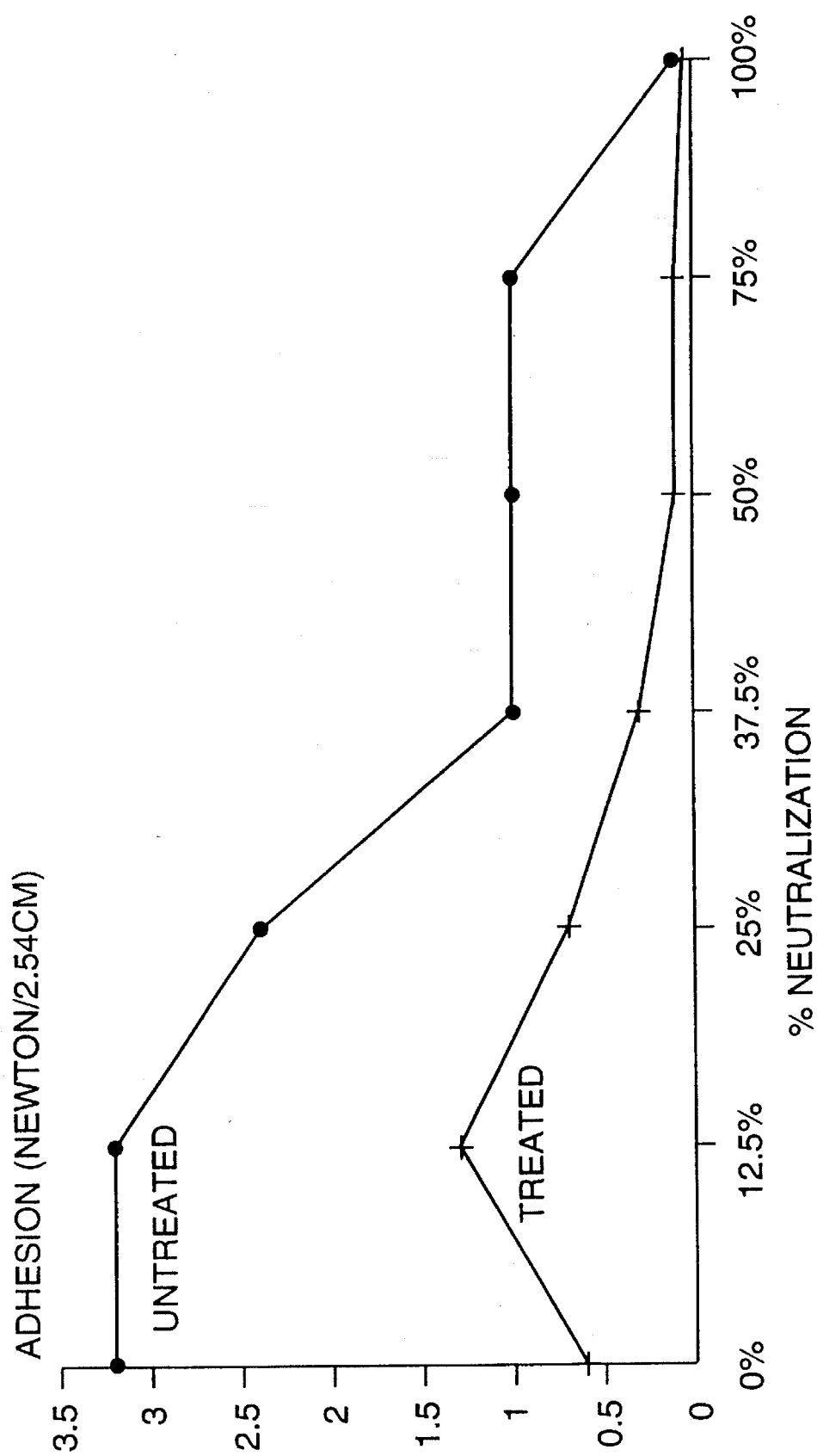
FIG. 6 is a graph of the initial adhesion of the indicator tapes of Examples 15–21 to untreated sterilization wrappers and to fluorochemically-treated polyester sterilization wrappers.
Figure 7:
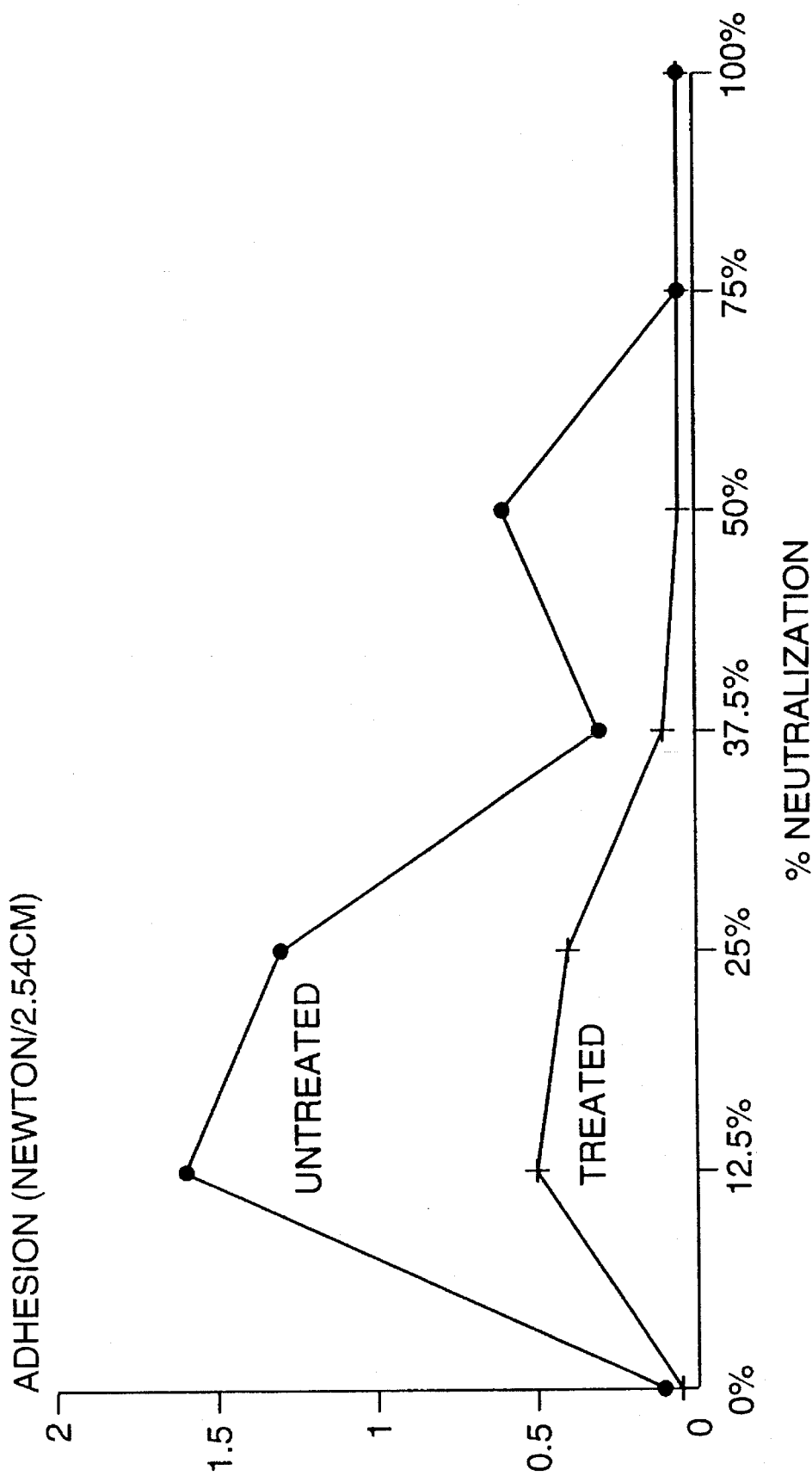
FIG. 7 is a graph of the initial adhesion of the indicator tapes of Examples 22–28 to untreated sterilization wrappers and to fluorochemically-treated polyester sterilization wrappers.

Tables 5 and 6, and FIGS. 6 and 7, show analogous results to those seen for Example indicator tapes Nos. 1–14. In addition, Table 5, shows that by reducing the amount of plasticizer included in the water-dispersible adhesives, that the number of useful indicator tapes has also been reduced. Specifically, only those indicator tapes using the PE-510 plasticizer, and with neutralization levels between 0% and 25% displayed sufficient initial adhesion to maintain the untreated wrappers in a closed position prior to sterilization. Thus, it appears that the degree of neutralization becomes a more important factor at reduced plasticizer levels. Furthermore, Table 5 shows that once the indicator tape has been sterilized, that its backing strength and post-sterilization adhesion are sufficient in all but one instance to keep the untreated wrapper closed, and withstand the normal handling associated with the transfer and storage of wrapped package.

Table 6 was not compared with respect to closure et al. because initial adhesion values were too low on the treated wrappers.

Comparative Example 29

A transfer adhesive (#905 Repulpable Flying Splice Tape";3M, St. Paul, Minn.) supplied at 0.05 mm (2 mils) thickness was laminated to the Kraft paper backing described in Example Indicator Tape Nos. 1–14. Initial adhesion to untreated wrappers was 2.6 Newton/2.54 cm and Post-sterilization adhesion was 2.9 Newton/2.54 cm. Comparative Example Indicator Tape No. 29 passed the Pre-sterilization Wrapper Closure Test T(0) with edge lift. Comparative Example 29 also passed the Post-sterilization Wrapper Closure Test T(A), Dispersibility of the pressure sensitive adhesive coating, and maintenance of closed wrapped bundles dropped from 38 cm and 91.5 cm using T-180 untreated cotton wrappers. For WrapPel™ 2 fluorochemically-treated wrappers the initial adhesion was 0.6 Newton/2.54 cm and 3.9 Newton/2.54 cm for post-sterilization adhesion. The initial adhesion was so low that further testing was not done. However, this adhesive was improperly reacted with the ink system used as the sterilization indicator. In particular, the adhesive caused the ink system to change color when in roll form. The phenomenon is believed to be due to the fact that the neutralizing agent in the adhesive is catalyzing the ink reaction prior to sterilization.

Comparative Examples 30–43

For comparison purposes the pressure sensitive adhesives in the solvent system from Example Indicator Tape Nos. 15–18 were coated at the same coating weight on a 8 lb basis weight, water dispersible tissue paper (8# Crystex Tissue Paper"; Crystal Paper Company, Middletown, Ohio).

Table 7 shows the initial adhesion, post-sterilization adhesion, pre-sterilization wrapper closure, post-sterilization wrapper closure, and dispersibility of the indicator tapes of Comparative Examples 30–43 on untreated 100% cotton wrappers. Table 8 shows the initial adhesion and post-sterilization adhesion of the indicator tapes of Comparative Examples 30–43 on fluorochemically-treated polyester wrappers (WrapPel™ 2).

TABLE 7

Initial adhesion, post-sterilization, pre-sterilization wrapper closure (T(o)), post-sterilization wrapper closure (T(A)), dispersibility of pressure sensitive adhesive coating, and maintenance of closed wrapped bundles dropped from 38 cm and 91.5 cm for Example Indicator Tapes Nos. 30–43 using T-180 untreated wrappers.

| Comp Ex. No. | Initial Adhesion (Newton/2.54 cm) | Post-Sterilize Adhesion (Newton/2.54 cm)[a] | Wrapper Closure T(o) (pass-/fail)[b] | Wrapper Closure T(A) (pass/fail)[b] | Drop Test @ 38 cm (pass/fail)[b] | Drop test @ 91.5 cm (pass/fail)[b] | Dispersibility (pass/fail) |
|---|---|---|---|---|---|---|---|
| 30 | 2.5 | 3.5 B | P | P-T | F-T | F-T | P |
| 31 | 2.4 | 3.2 B | P | F-T | F-T | F-T | P |
| 32 | 1.6 | 4.8 B | P | F-T | F-T | F-T | P |
| 33 | 1.4 | 4.0 B | P | P | F-T | F-T | P |
| 34 | 0.8 | 3.6 B | P | P | P | F-T | P |
| 35 | 1.7 | 6.2 B | P | P | P-T | F-T | P |
| 36 | 0.6 | 4.5 B | P | P-T | F-T | F-T | P |
| 37 | 0.1 | 1.7 B | P-E | F-T | F-T | F-T | P |
| 38 | 1.3 | 4.0 B | P | P | F-T | F-T | P |
| 39 | 1.4 | 5.0 B | P | P | F-T | F-T | P |
| 40 | 0.7 | 10.6 B | P | P | P-T | F-T | P |
| 41 | 0.7 | 4.4 B | P | P | F-T | F-T | P |
| 42 | 0.1 | 3.7 B | P-E | P | F-T | F-T | P |
| 43 | 0.1 | 3.1 B | F-P | P-T | F-T | F-T | P |

[a]B = tissue paper backing broke during adhesion testing
[b]P = pass, PE = pass with edge lift, PT = pass with some tear in backing, FP = failed popped off, FT = failed by torn backing

TABLE 8

Initial adhesion and post-sterilization adhesion for Comparative Example Indicator Tapes Nos. 30–43 on WrapPel 2 ™ fluorochemically-treated wrappers.

| | | |
|---|---|---|
| 30 | 0.5 | 1.2B |
| 31 | 0.5 | 1.2B |
| 32 | 0.7 | 2.1B |
| 33 | 0.4 | 1.2 |
| 34 | 0.2 | 0.9 |
| 35 | 0.1 | 1.6B |
| 36 | >0.1 | 1.0B |
| 37 | >0.1 | 0.8B |
| 38 | 0.4 | 1.5B |
| 39 | 0.4 | 1.1 |
| 40 | 0.1 | 1.5 |
| 41 | 0.2 | 1.3 |
| 42 | >0.1 | 1.4 |
| 43 | >0.1 | 1.1 |

[a]B = tissue paper backing broke during adhesion testing

Tables 7 and 8 show analogous results to those results seen for initial adhesion for Example indicator tapes 15–28. The pre-sterilization wrapper closure results were improved when compared to Example indicator tapes 15–28, as the conformability of the tissue paper backing helped to prevent the edge lift and popping from occurring. Post-sterilization wrapper closure tests were worse when compared to Example indicator tapes 15–28, as Examples 30–43 showed a greater degree of failure due to the low strength tissue backing becoming torn during the pressurization of the sterilization cycle. This lack of backing strength is further illustrated in the drop test data. Only one sample survived the 38 cm drop test, and all samples failed at the 91.5 cm drop level. Table 8 was not compared with respect to wrapper closure, dispersibility and drop tests, because initial adhesion values were too low on the treated wrappers.

Comparative Examples 44–45

The pressure sensitive adhesive in solvent system from Example 17 (Table 4) was coated on an unoriented polyvinyl alcohol backing, 0.06 mm (2.5 mils) thick (VINEX™ Polyvinyl Alcohol Film; Air Products and Chemicals, Inc., Allentown, Pa.) at a coating weight of 0.68 g/154.8 cm$^2$ for Comparative Example 44. A transfer 0adhesive (No. 905, Repulpable Flying Splice Tape; 3M Company, St. Paul, Minn.) was laminated on the same vinyl backing as Comparative Example 44 to yield Comparative Example 45. Table 9 shows the initial adhesion, post-sterilization adhesion, pre-sterilization wrapper closure, post-sterilization wrapper closure, dispersibility, drop test results at 38 cm and 91.5 cm for the indicator tapes of Comparative Examples 44–45. The results show that the vinyl dispersible backing melted under sterilization conditions.

cally-treated polyester wrappers respectively.

TABLE 10

Formulation of water dispersible, pressure sensitive adhesives coated on Example Indicator Tapes Nos. 46–55.

| Ex. No. | Copolymer BA/AA (parts) | Plasticizer PE-510 (parts) | Tackifier Foral AX (parts) | Neutralization (%) | Solids (%) |
|---|---|---|---|---|---|
| 46 | 100 | 120 | 25 | 0 | 35.0 |
| 47 | 100 | 120 | 25 | 12.5 | 35.0 |
| 48 | 100 | 120 | 25 | 25 | 35.0 |
| 49 | 100 | 120 | 25 | 37.5 | 35.0 |
| 50 | 100 | 120 | 25 | 50 | 35.0 |
| 51 | 100 | 120 | 25 | 75 | 35.0 |
| 52 | 100 | 120 | 25 | 100 | 35.0 |
| 53 | 100 | 105 | 25 | 25 | 35.0 |
| 54 | 100 | 135 | 25 | 25 | 35.0 |
| 55 | 100 | 150 | 25 | 25 | 35.0 |

TABLE 9

Initial adhesion, post-sterilization adhesion, pre-sterilization wrapper closure (T(o)), post-sterilization wrapper closure (T(A)), dispersibility of pressure sensitive adhesive coating, and maintenance of closed wrapped bundles dropped from 38 cm and 9.15 cm for Comparative Example Indicator Tapes Nos. 44–45 using T-180 untreated wrappers.

| Comp Ex. No. | Initial Adhesion (Newton/2.54 cm) | Post-Sterilize Adhesion (Newton/2.54 cm) | Wrapper Closure T(O) (pass/fail) | Wrapper Closure T(A) (pass/fail) | Dispersibility (pass/fail) | Drop Test @ 38 cm (pass/fail) | Drop Test @ 91.5 cm (pass/fail) |
|---|---|---|---|---|---|---|---|
| 44 | 1.2 | Melt | P-E | Melt | Pass | Melt | Melt |
| 45 | 1.8 | Melt | P-E | Melt | Pass | Melt | Melt |

EXAMPLES 46–55

The pressure sensitive adhesives in the solvent system were coated on Kraft paper at 0.68 g/154.8 cm$^2$. The amount of PE-510 plasticizer was varied to determine its effect on performance properties. Table 10 shows the formulations of water-dispersible, pressure sensitive adhesives coated on Example indicator tapes Nos. 46–55. Tables 11 and 12 show the initial adhesion, post-sterilization adhesion, pre-sterilization wrapper closure, post-sterilization wrapper closure and dispersibility of the indicator tapes of Examples 46–55 on untreated 100% cotton wrappers and on fluorochemi-

TABLE 11

Initial adhesion, post-sterilization adhesion, pre-sterilization wrapper closure (T(o)), post-sterilization wrapper closure (T(A)), and dispersibility of pressure-sensitive adhesive coating for Example Indicator Tapes Nos. 46–55 on untreated wrappers.

| Ex. No. | Initial Adhesion (Newton/2.54 cm) | Post-Sterilized Adhesion (Newton/2.54 cm) | Wrapper Closure T(o) (pass/fail)[a] | Wrapper Closure T(A) (pass/fail) | Dispersibility (pass/fail) |
|---|---|---|---|---|---|
| 46 | .8 | 2.1 | P | P | P |
| 47 | 2.9 | 1.3 | P | P | P |
| 48 | 2.4 | 1.5 | P | P | P |
| 49 | 1.6 | 2.0 | P | P | P |
| 50 | .9 | 2.1 | P | P | P |
| 51 | .4 | 1.9 | P | P | P |
| 52 | .2 | 2.1 | P-E | P | P |

TABLE 11-continued

Initial adhesion, post-sterilization adhesion, pre-sterilization wrapper closure (T(o)), post-sterilization wrapper closure (T(A)), and dispersibility of pressure-sensitive adhesive coating for Example Indicator Tapes Nos. 46–55 on untreated wrappers.

| Ex. No. | Initial Adhesion (Newton/2.54 cm) | Post-Sterilized Adhesion (Newton/2.54 cm) | Wrapper Closure T(o) (pass/fail)[a] | Wrapper Closure T(A) (pass/fail) | Dispersibility (pass/fail) |
|---|---|---|---|---|---|
| 53 | 1.4 | 2.1 | P | P | P |
| 54 | 2.5 | 1.4 | P | P | P |
| 55 | 3.2 | 1.1 | P | P | P |

[a]P = pass, PE = pass with edge lift

TABLE 12

Initial adhesion, post-sterilization adhesion, pre-sterilization wrapper closure (T(o)), post-sterilization wrapper closure (T(A)), and dispersibility of pressure sensitive adhesive coating for Example Indicator Tapes Nos. 46–55 as WrapPel ™ 2 fluorochemically-treated wrappers.

| Ex. No. | Initial Adhesion (Newton/2.54 cm) | Sterilized Adhesion (Newton/2.54 cm) | Wrapper Closure T(o) (pass/fail)[a] | Wrapper Closure T(o) (pass/fail)[a] | Dispersibility (pass/fail) |
|---|---|---|---|---|---|
| 46 | .4 | 2.1 | F-C | P-E | P |
| 47 | .4 | 1.9 | P-E | P-E | P |
| 48 | .1 | 2.0 | F-C | P-E | P |
| 49 | .1 | 1.7 | F-C | F-P | P |
| 50 | >.1 | 1.8 | F-P | P-E | P |
| 51 | >.1 | 2.0 | F-P | P-E | P |
| 52 | >.1 | 2.0 | F-P | F-P | P |
| 53 | .3 | 2.7 | P-E | P-E | P |
| 54 | .4 | 2.0 | P-E | P-E | P |
| 55 | .6 | 1.9 | F-C | P-E | P |

[a]PE = pass with edge lift, FC = failed curled up, FP = failed popped off

Figure 8:
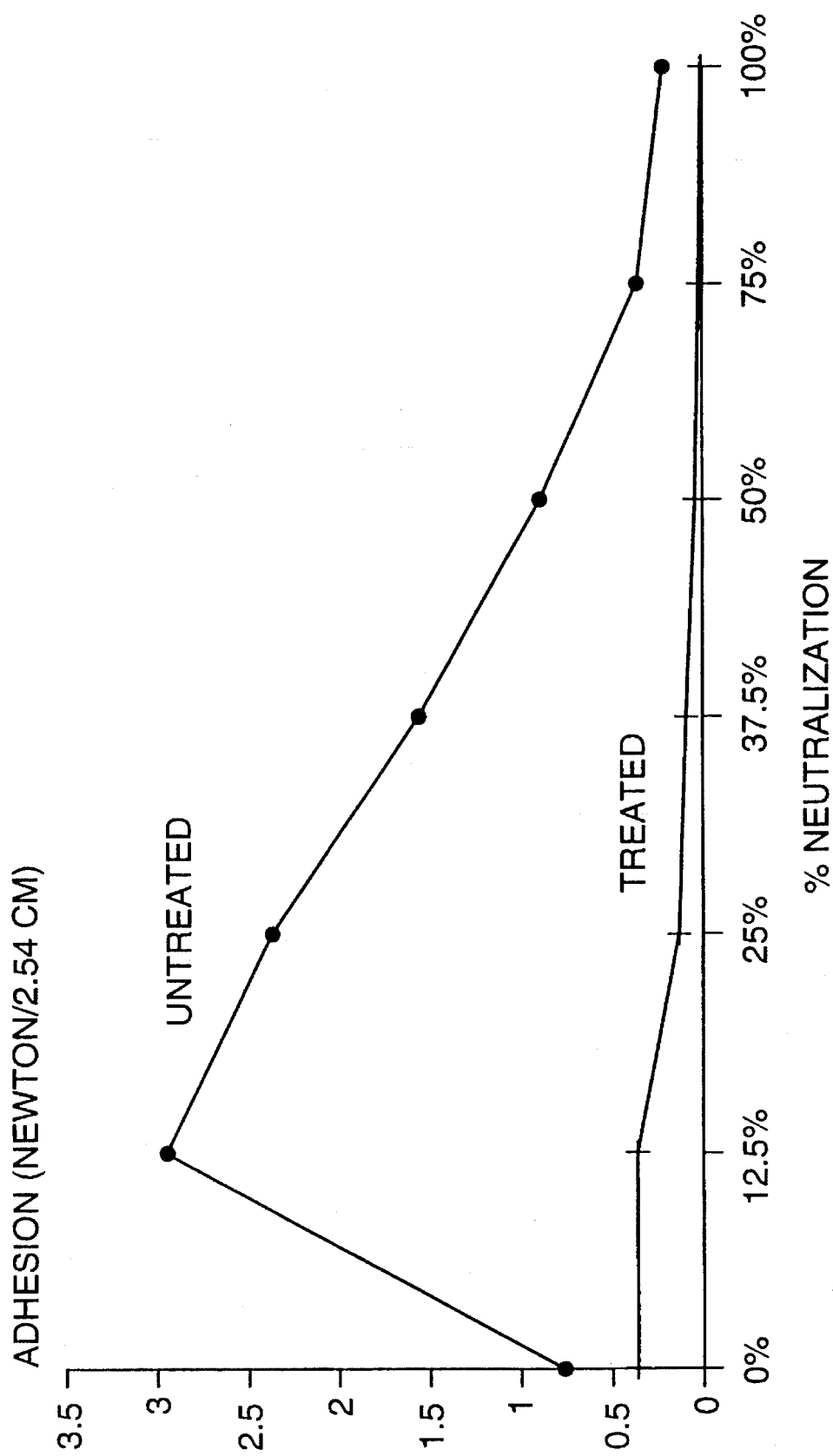
FIG. 8 is a graph of the initial adhesion of the indicator tapes of Examples 46–52 to untreated sterilization wrappers and to fluorochemically-treated polyester sterilization wrappers.

Tables 11 and 12 and FIG. 8 show Example indicator tapes 46–52 have analogous results to indicator tapes 1–7. However, Examples 46–52 show improved presterilization wrapper closure results on untreated wrappers. On treated wrappers Examples 46–52 also show analogous results to Examples 1–7, with only one example indicator tape (No. 47) performing adequately. Overall, it can be seen that edge lift is decreased, while overall performance is not diminished when increasing the plasticizer level in the adhesive composition up to 120 parts. These improved results take place even though coating weight has decreased from 0.68 g/154.8 cm$^2$ to 0.58 g/154.8 cm$^2$.

Figure 9:
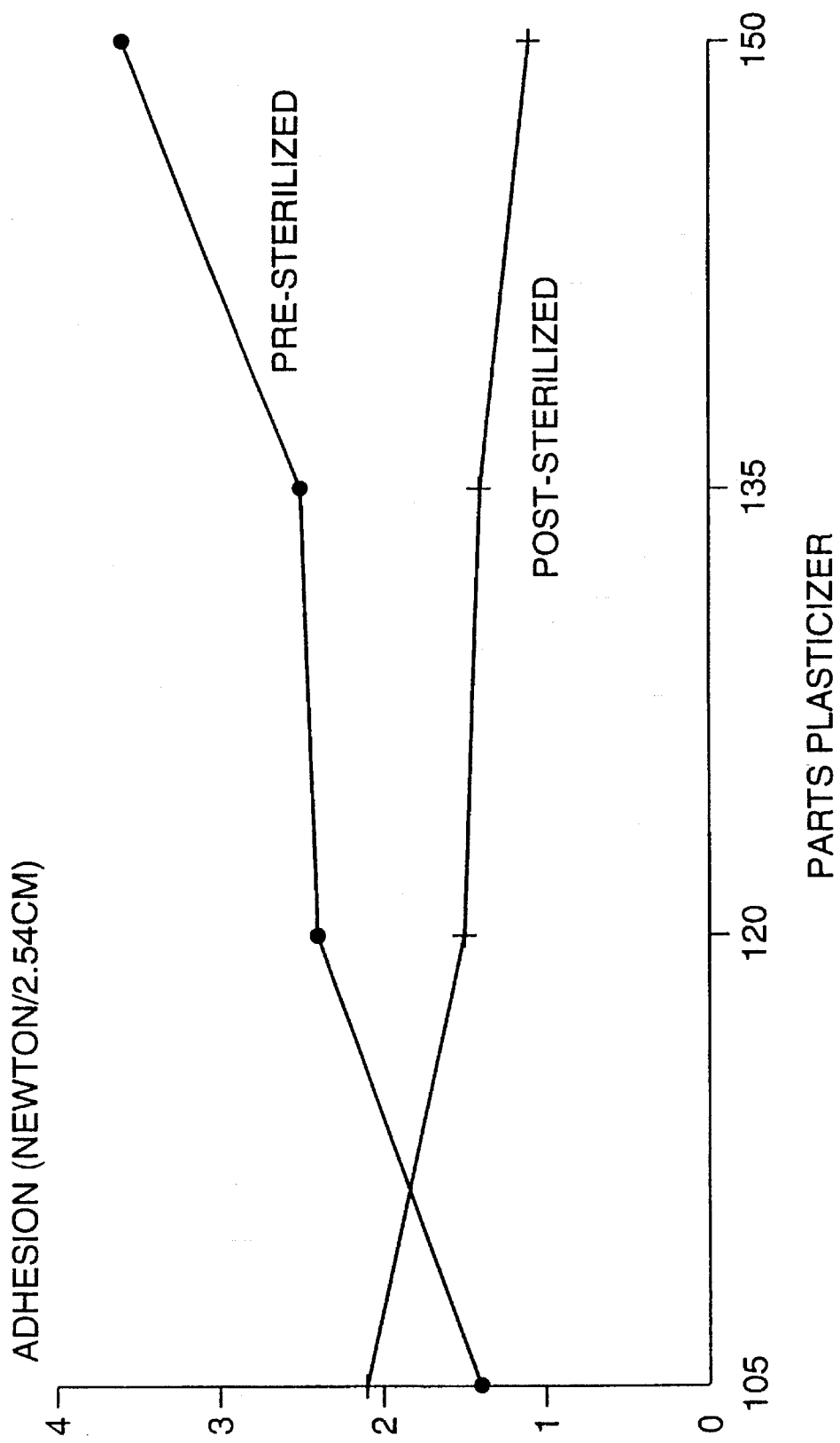
FIG. 9 is a graph of the pre-sterilized (initial) adhesion and post-sterilized adhesion versus parts plasticizer of Example indicator tapes Nos. 48 and 53–55 on untreated sterilization wrappers.

For examples 48 and 53–55, Table 11 and FIG. 9 show that on untreated wrappers initial adhesion increases with increasing plasticizer level, while post sterilized adhesion decreased with increasing plasticizer level. However, all Examples formed acceptable indicator tapes.

Figure 10:
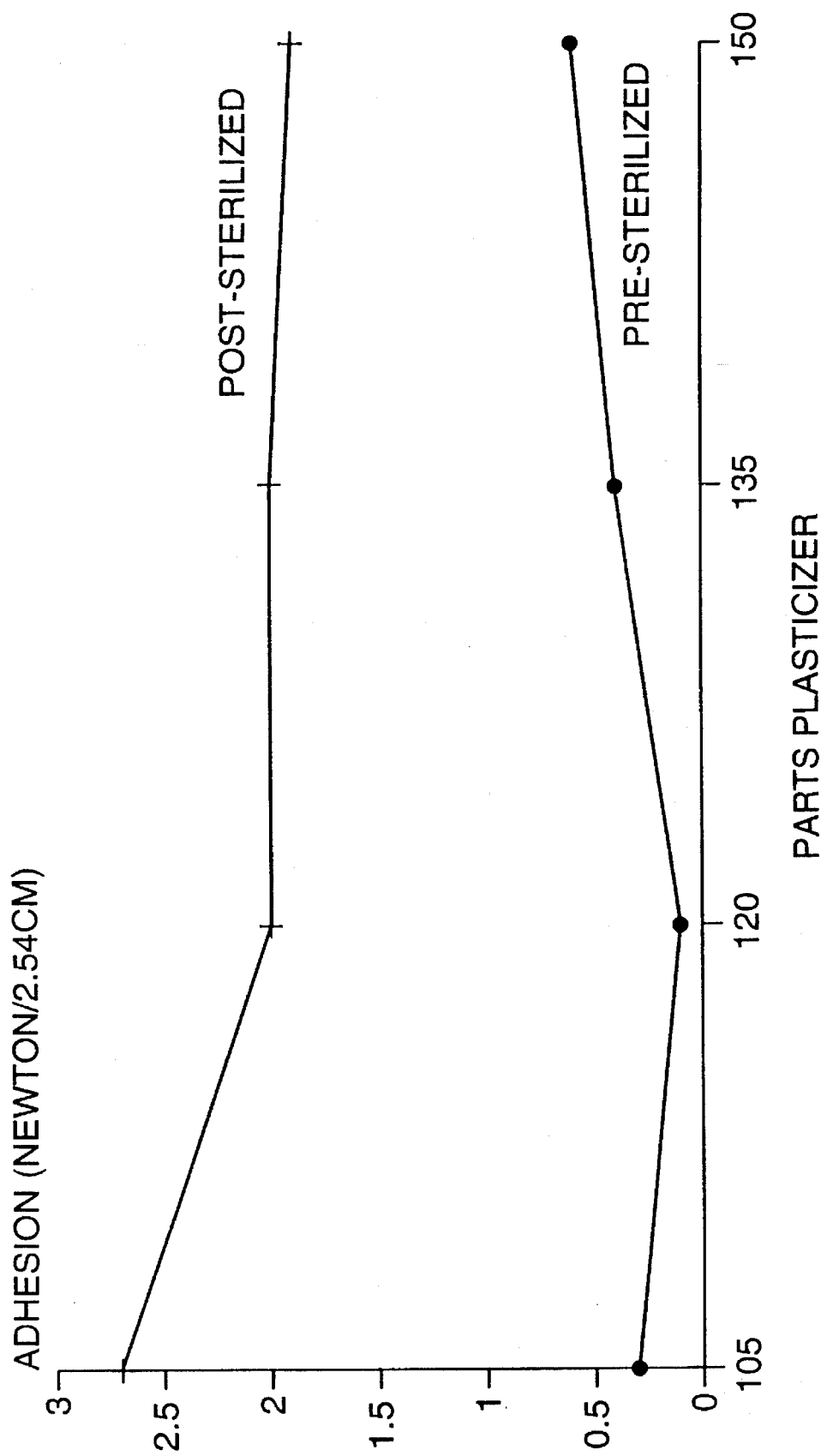
FIG. 10 is a graph of the pre-sterilized (initial) adhesion and post-sterilized adhesion versus parts plasticizer of Example indicator tapes Nos. 48 and 53–55 on fluorochemically-treated polyester sterilization wrappers.

Table 12 and FIG. 10 show that on treated wrappers, initial adhesion increases with increasing plasticizer level, while post sterilized adhesion decreased with increasing plasticizer level. However, only Examples 53 and 54 kept the bundle closed prior to sterilization.

Comparative Example 56

A commonly used indicator tape for wrapper closure (No. 1222 autoclave tape; 3M Company), was used for comparison of performance properties on untreated wrappers and treated wrappers. On untreated wrappers, initial adhesion was 1.2 N/2.54 cm, post-sterilization adhesion was 1.9 N/2.54 cm, and the indicator tape passed pre and post-sterilization wrapper closure tests. On treated wrappers, initial adhesion was 0.3 N/2.54 cm, post-sterilization adhesion was 0.6 N/2.54 cm, and the indicator tape failed both pre- and post-sterilization wrapper closure tests. The adhesive for the indicator tape failed to disperse during laundering for both treated and untreated wrappers.

EXAMPLES 57–58

The pressure sensitive adhesive described for Example indicator tape No. 48 was coated on Kraft paper at 0.87 g/154.8 cm$^2$ for Example 57, and at 1.04 g/154.8 cm$^2$ for Example 58. These Examples were done to show the effect of increased coating weight on performance properties. Example indicator tape No. 57 on untreated wrappers had initial adhesion of 2.9 N/2.54 cm and post-sterilization adhesion of 1.8 N/2.54 cm. Example indicator tape No. 58 on untreated wrappers had initial adhesion of 3.2 N/2.54 cm and post-sterilization adhesion of 2.2 N/2.54 cm.

Example indicator tape No. 57 on treated wrappers had initial adhesion of 0.7 N/2.54 cm and post-sterilization adhesion of 2.2 N/2.54 cm. Example indicator tape No. 58 on treated wrappers had initial adhesion of 1.1 N/2.54 cm and post-sterilization adhesion of 4.2 N/2.54 cm.

The Example indicator tape Nos. 57 and 58 passed the pre- and post-sterilization wrapper closure test on untreated wrappers. On treated wrappers, both Examples 57 and 58 passed pre- and post-sterilization wrapper closure with edge lift. Both Example indicator tapes passed dispersibility of the pressure sensitive adhesive on untreated and treated wrappers.

Figure 11:
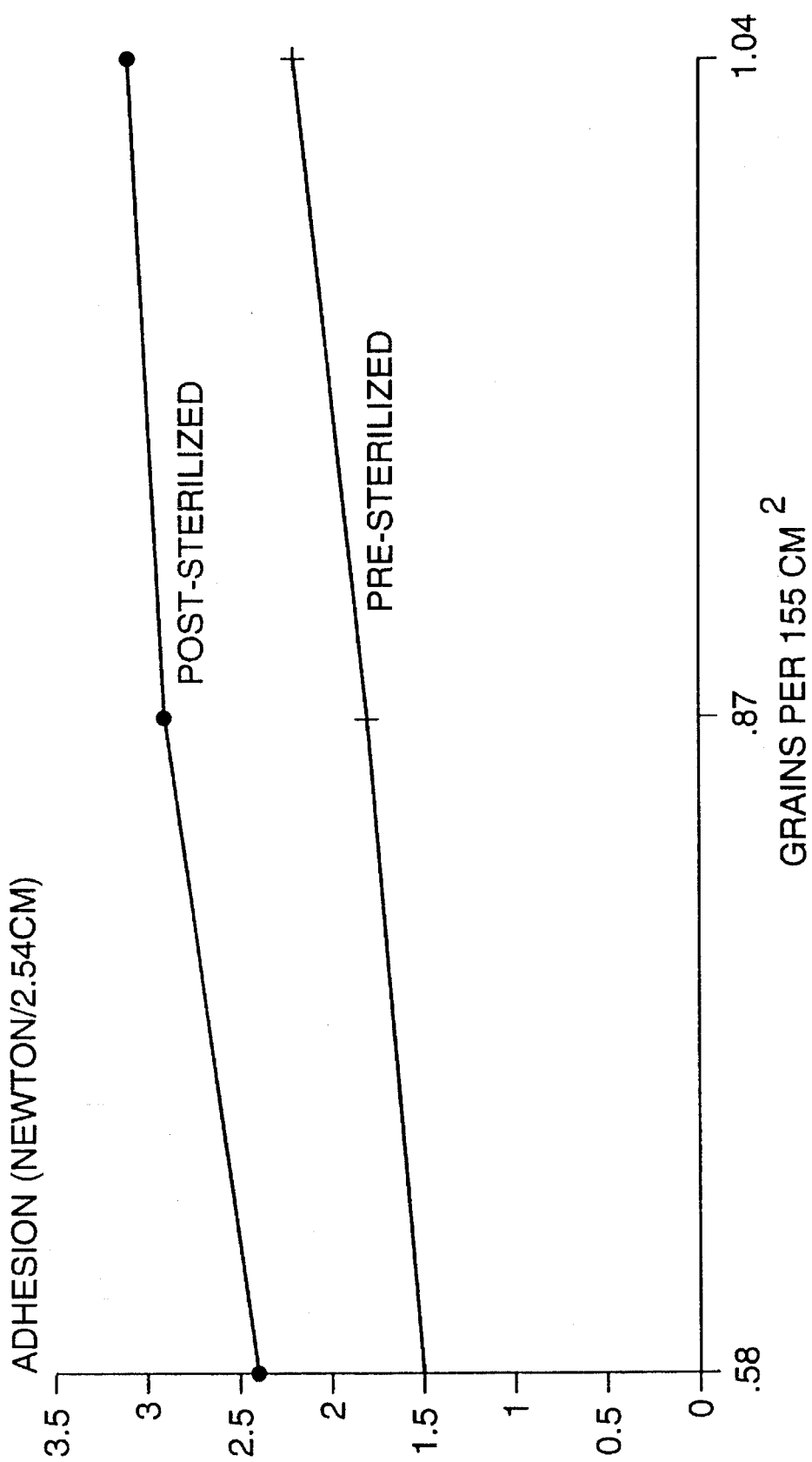
FIG. 11 is a graph of the pre-sterilized (initial) adhesion and post-sterilized adhesion versus the coating weight of adhesive of Example indicator tapes Nos. 48 and 57–58 on untreated sterilization wrappers; and, FIG. 12 is a graph of the pre-sterilized (initial) adhesion and post-sterilized adhesion versus the coating weight of adhesive of Example indicator tapes Nos. 48 and 57–58 on fluorochemically-treated polyester sterilization wrappers.
Figure 12:
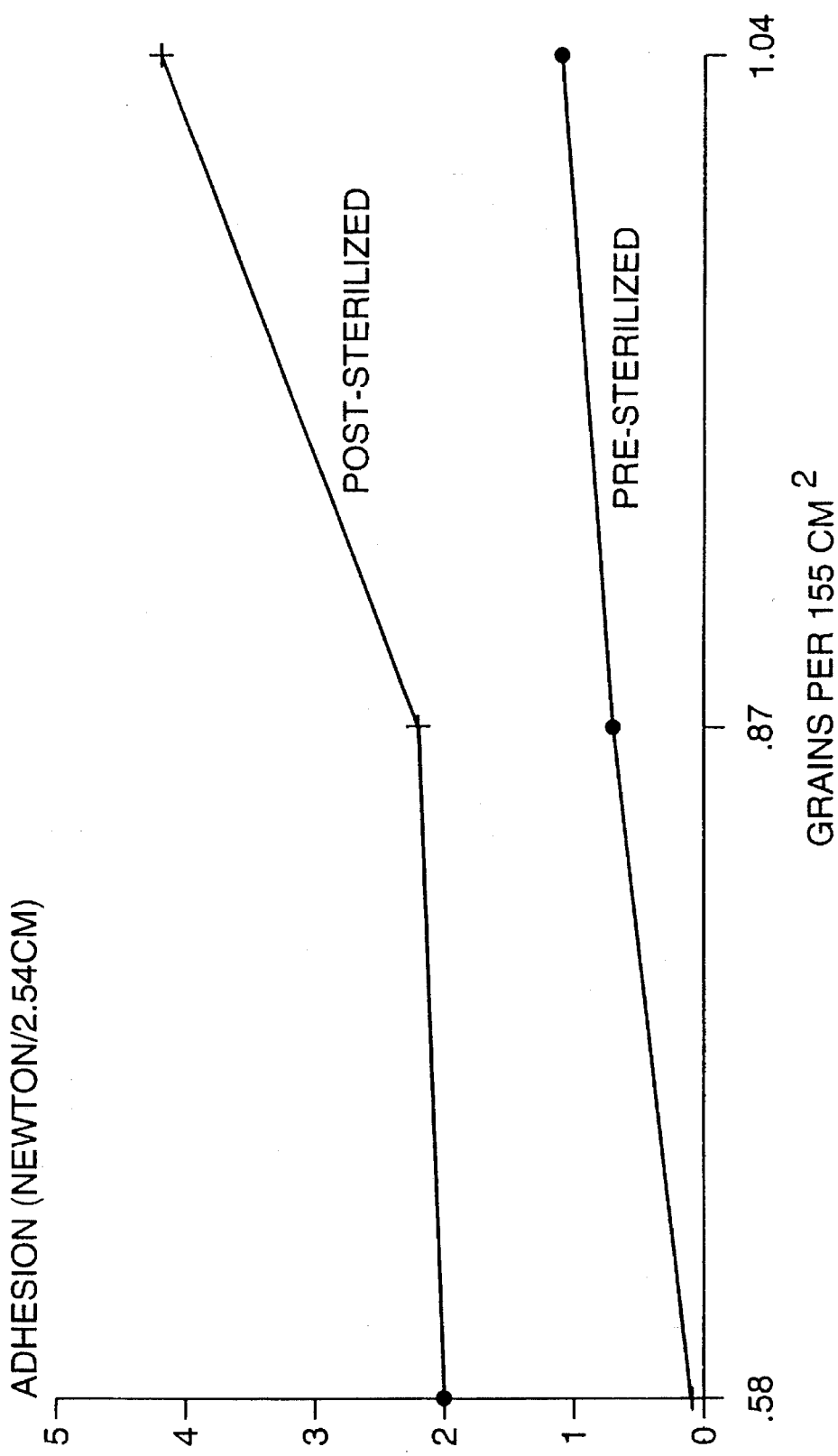

FIG. 11 shows for Examples 48, 57 and 58, that increasing coating weight increased initial adhesion, post-sterilized adhesion, and improved pre- and post-sterilization wrapper closure results on untreated wrappers. FIG. 12 shows for Examples 48, 57 and 58, that increasing coating weight increased initial adhesion, post-sterilized adhesion, and improved pre- and post-sterilization wrapper closure results on treated wrappers. The higher coating weight at this formulation allows for two acceptable indicator tapes Nos. 57 and 58 for treated wrappers to be formed.

EXAMPLE 59 AND COMPARATIVE EXAMPLE 60

Example indicator tape No. 59 was made as described for Example indicator tape No. 48. Comparative Example indicator tape No. 60 was a commonly used indicator tape for ethylene oxide sterilization (No. 1224, ethylene oxide indicator tape; 3M Company) These example tapes were tested as in Examples 1–14, except that they were sterilized in a No. 4XL Ethylene Oxide Sterilizer (3M Company) using the cold cycle and a 3M brand Steri-Gas™ No. 4–100 ethylene oxide cartridge.

On untreated wrappers, Example indicator tape No. 59 had initial adhesion of 2.4 N/2.54 cm and post-sterilization adhesion of 6.0 N/2.54 cm. Comparative Example indicator tape No. 60 on untreated wrappers had initial adhesion of 0.9 N/2.54 cm and post-sterilization adhesion of 3.5 N/2.54 cm. Example indicator tape No. 59 and Comparative Example indicator tape No. 60 on untreated wrappers passed pre- and post-sterilization wrapper closure test.

On treated wrappers, Example indicator tape No. 59 had initial adhesion of 0.1 N/2.54 cm and post-sterilization adhesion of 5.6 N/2.54 cm. Comparative Example indicator tape No. 60 on treated wrappers had initial adhesion of 0.1 N/2.54 cm and post-sterilization adhesion of 3.5 N/2.54 cm. Example indicator tape No. 59 and Comparative Example indicator tape No. 60 on treated wrappers passed pre- and post-sterilization wrapper closure test with edge lift.

Example indicator tape No. 59 passed the dispersibilty test, while Comparative Example indicator tape No. 60 failed.

Throughout the present application, the following abbreviations have been employed.

| | Acrylate Monomer |
|---|---|
| BA | butyl acrylate |
| | Vinyl Carboxylic Acid Monomer |
| AA | acrylic acid |
| | Tackifier |
| AX | colophony acid rosin tackifier, available for Hercules Corp. under the trademark "Foral AX" |
| | Plasticizer |
| PE-510 | poly(oxy-1,2-ethandiyl), alpha-(nonylphenyl)-omega-hydroxy-phosphate, available from Rhone Poulenc under the trademark "Rhodafac PE-510" |
| RE-410 | poly(oxy-1,2-ethandiyl), alpha-(nonylphenyl)-omega-hydroxy-phosphate, available from Rhone Poulenc under the trademark "Rhodafac RE-410" |
| | Neutralization (%) |
| | Percent copolymer acid neutralized with potassium hydroxide (KOH). |
| | Solvent |
| | An Ethyl Acetate/Methanol/Water in a weight ratio of 80/15/5. |
| | Testing Wrappers |
| WrapPel™ 2 | 100% treated polyester commercially available from Standard Textile Co., Cincinnati, OH |
| T-180 | 100% cotton T-180 Surgical wrapper commercially available from American Linen Supply Co., St. Paul, MN |

While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A method of making an indicator tape comprising:

(a) providing a non-water-dispersible backing having opposing sides;

(b) printing a sterilization indicator comprising an indicator ink in combination with a binder on one of the sides of the backing, said indicator ink being capable of undergoing a color change when exposed to sterilization conditions; and, (c) coating a moisture-resistant, water-dispersible, pressure sensitive adhesive on the opposing side of the backing.

\* \* \* \* \*